(12) United States Patent
Eltorai

(10) Patent No.: US 12,246,189 B2
(45) Date of Patent: *Mar. 11, 2025

(54) METHOD, SYSTEM, AND DEVICES OF SAFE, ANTIMICROBIAL LIGHT-EMITTING CATHETERS, TUBES, AND INSTRUMENTS

(71) Applicant: Lumen Catheters, LLC, Marlborough, MA (US)

(72) Inventor: Adam E. M. Eltorai, Marlborough, MA (US)

(73) Assignee: Luminary, LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/373,803

(22) Filed: Sep. 27, 2023

(65) Prior Publication Data

US 2024/0024698 A1 Jan. 25, 2024

Related U.S. Application Data

(63) Continuation of application No. 15/832,242, filed on Dec. 5, 2017, now Pat. No. 11,806,549.

(51) Int. Cl.
*A61N 5/06* (2006.01)
*A61N 5/067* (2006.01)
(Continued)

(52) U.S. Cl.
CPC .......... *A61N 5/0624* (2013.01); *A61N 5/0601* (2013.01); *A61M 25/0043* (2013.01); *A61M 25/0097* (2013.01); *A61M 25/10* (2013.01); *A61N 2005/0602* (2013.01); *A61N 2005/0604* (2013.01); *A61N 2005/061* (2013.01);
(Continued)

(58) Field of Classification Search
CPC .... A61N 5/0624; A61N 5/0601; A61N 5/067; A61N 2005/063; A61N 2005/0602; A61N 2005/061; A61M 25/0097; A61M 25/0043
See application file for complete search history.

(56) References Cited

U.S. PATENT DOCUMENTS 5,776,174 A * 7/1998 Van Tassel ........... A61N 5/0601
606/15
7,131,963 B1 * 11/2006 Hyde ..................... A61B 17/22
604/509

(Continued)

*Primary Examiner* — Paula J Stice
(74) *Attorney, Agent, or Firm* — Armis IP Law, LLC

(57) ABSTRACT

A light-emitting, antimicrobial tuber, instrument or catheter includes a thin, flexible tube having an optically transparent wall; and a light transmitter configured and arranged to emit light through the tube, which may be ultraviolet C (UVC) irradiation, photodynamic therapy (PDT), violet-blue light therapy, and other light-based therapies. In one embodiment, violet-blue light from 400-500 nm in wavelength, such as 405 nm, for instance, is used. The device is used on a patient and a therapeutic amount of light is administered to the patient, thereby reducing the risk of infections being transmitted from the instrument, tube or catheter to the patient, generally. The device may be configured for use in the urinary tract or as intravascular, and may be indwelling or temporary. Light may be administered for the duration of use or another time period effective to halt, inhibit, or reduce microbial or fungal growth.

25 Claims, 42 Drawing Sheets

(51) Int. Cl.
  *A61M 25/00* (2006.01)
  *A61M 25/10* (2013.01)

(52) U.S. Cl.
  CPC  *A61N 2005/063* (2013.01); *A61N 2005/0661* (2013.01); *A61N 2005/0663* (2013.01); *A61N 5/067* (2021.08)

(56) References Cited

U.S. PATENT DOCUMENTS

| | | | |
|---|---|---|---|
| 7,351,231 B2 * | 4/2008 | Young | A61M 25/0097 |
| | | | 604/506 |
| 2002/0183301 A1 | 12/2002 | Rychnovsky | |
| 2004/0039242 A1 | 2/2004 | Tolkoff et al. | |
| 2004/0093044 A1 | 5/2004 | Rychnovsky et al. | |
| 2007/0260295 A1 * | 11/2007 | Chen | A61N 5/062 |
| | | | 607/88 |
| 2008/0051736 A1 | 2/2008 | Rioux et al. | |
| 2009/0112196 A1 | 4/2009 | Rabiner et al. | |
| 2010/0241198 A1 | 9/2010 | Klepper | |
| 2012/0161032 A1 | 6/2012 | Arcand et al. | |
| 2013/0123579 A1 | 5/2013 | Adams et al. | |
| 2014/0235942 A1 | 8/2014 | Hellstrom et al. | |
| 2015/0190649 A1 | 7/2015 | Gelfand et al. | |
| 2015/0231287 A1 | 8/2015 | Lin et al. | |
| 2016/0151639 A1 | 6/2016 | Scharf et al. | |
| 2016/0278863 A1 | 9/2016 | Arai et al. | |
| 2016/0346565 A1 * | 12/2016 | Rhodes | A61F 13/0266 |
| 2017/0128742 A1 | 5/2017 | Rabiner et al. | |

* cited by examiner

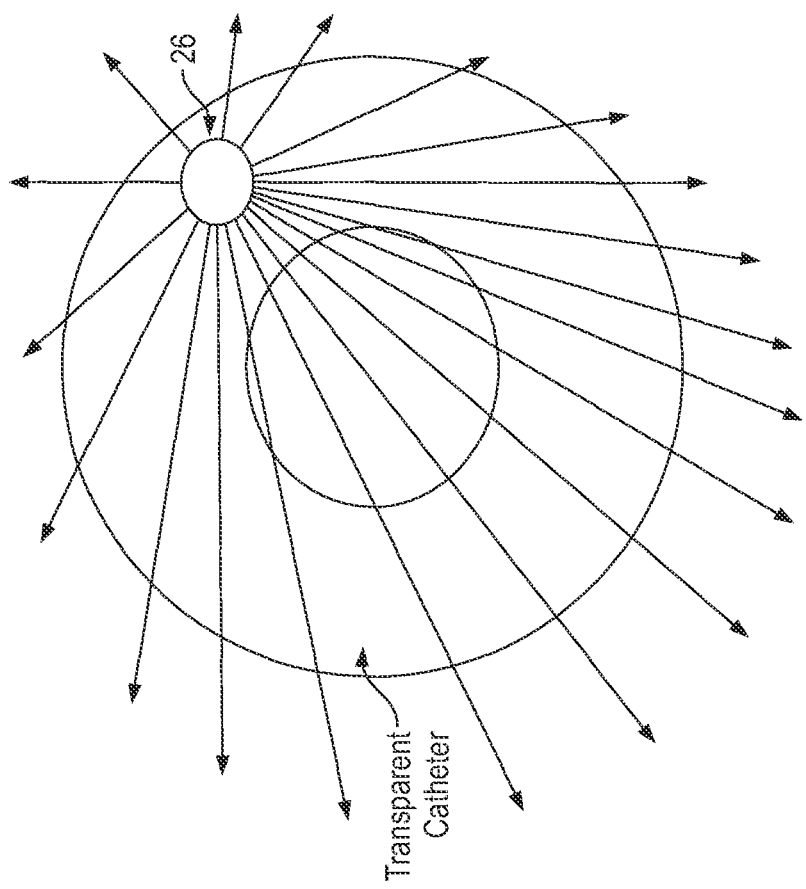

100 ⟶

102 — Providing a catheter, comprising a thin, flexible tube having an optically transparent wall; and a light transmitter configured and arranged to emit light through the tube

104 — Catheterizing a patient with the catheter; and

106 — Administering a therapeutic amount of light with the light transmitter

108 — Removing the catheter from the patient

FIG. 4

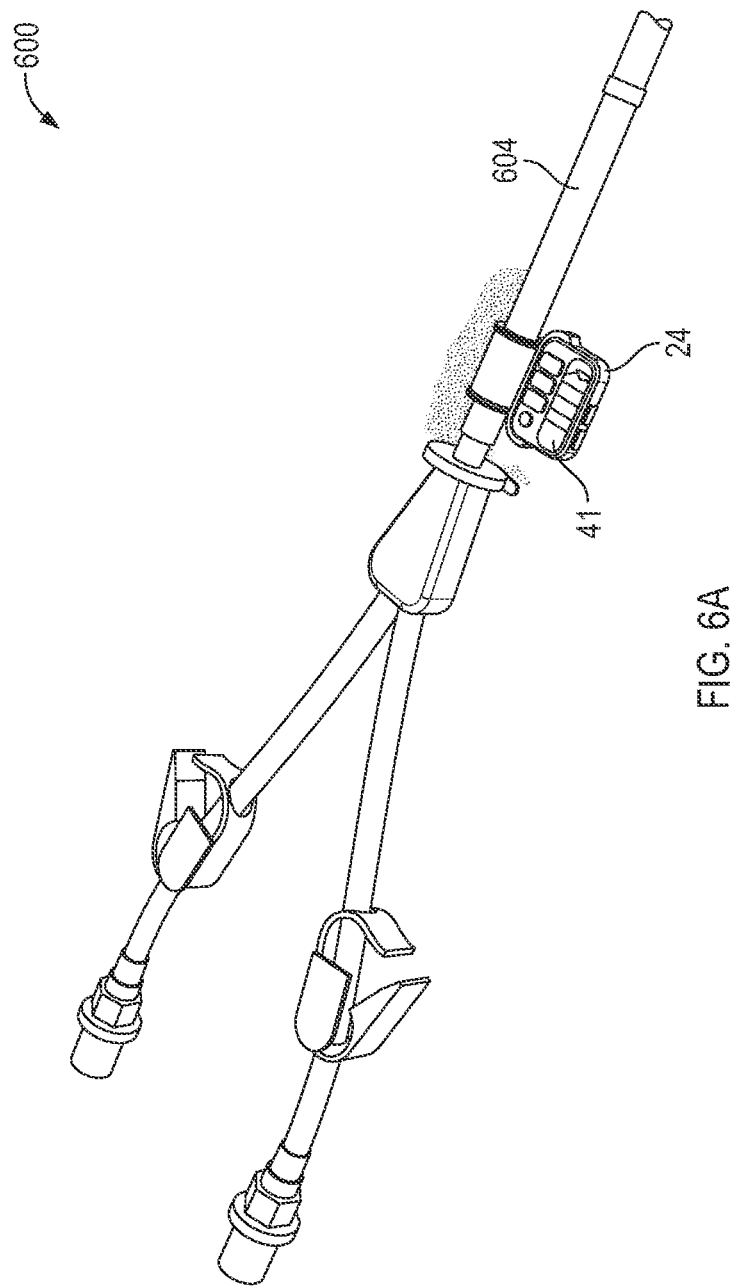

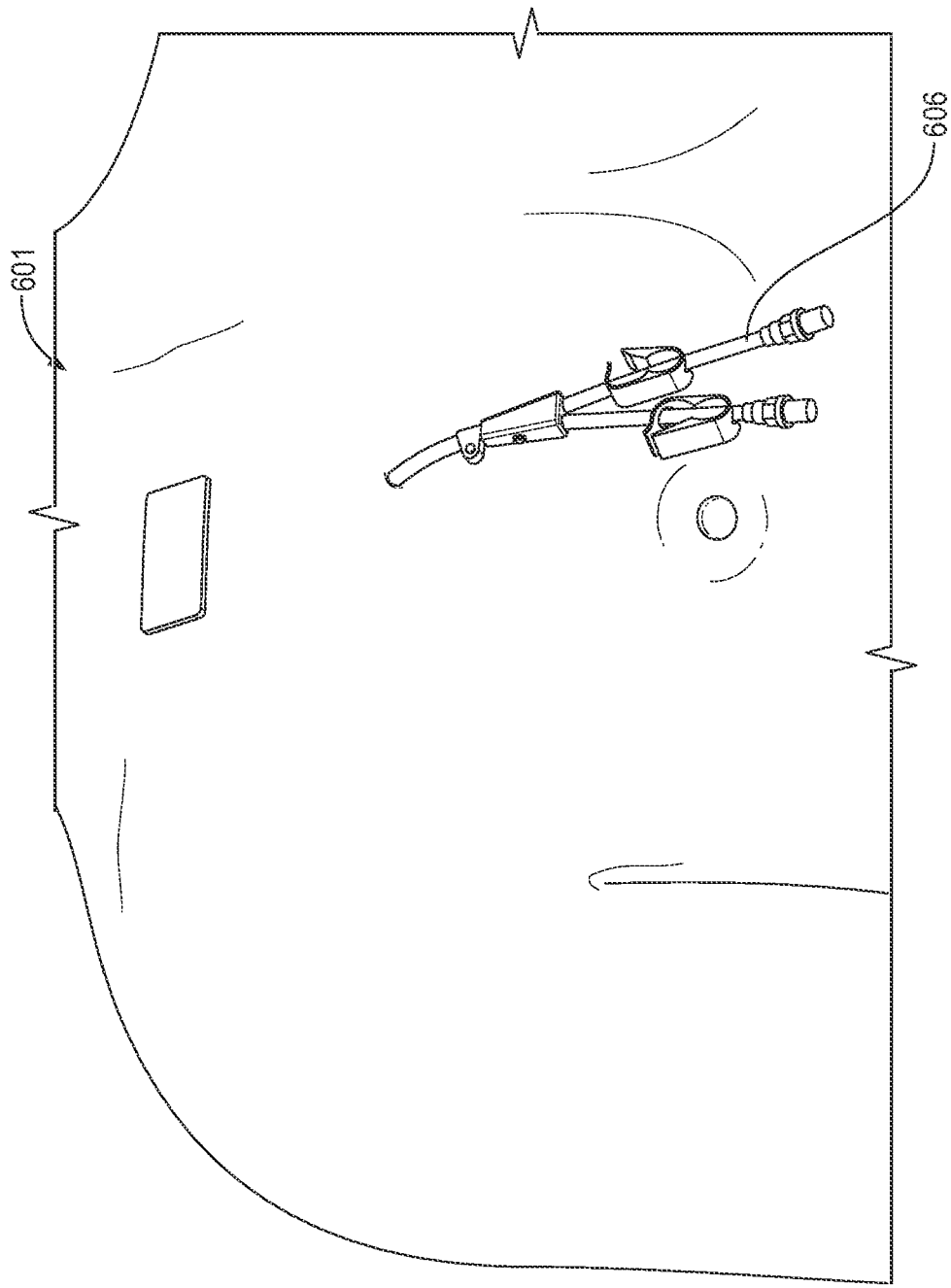

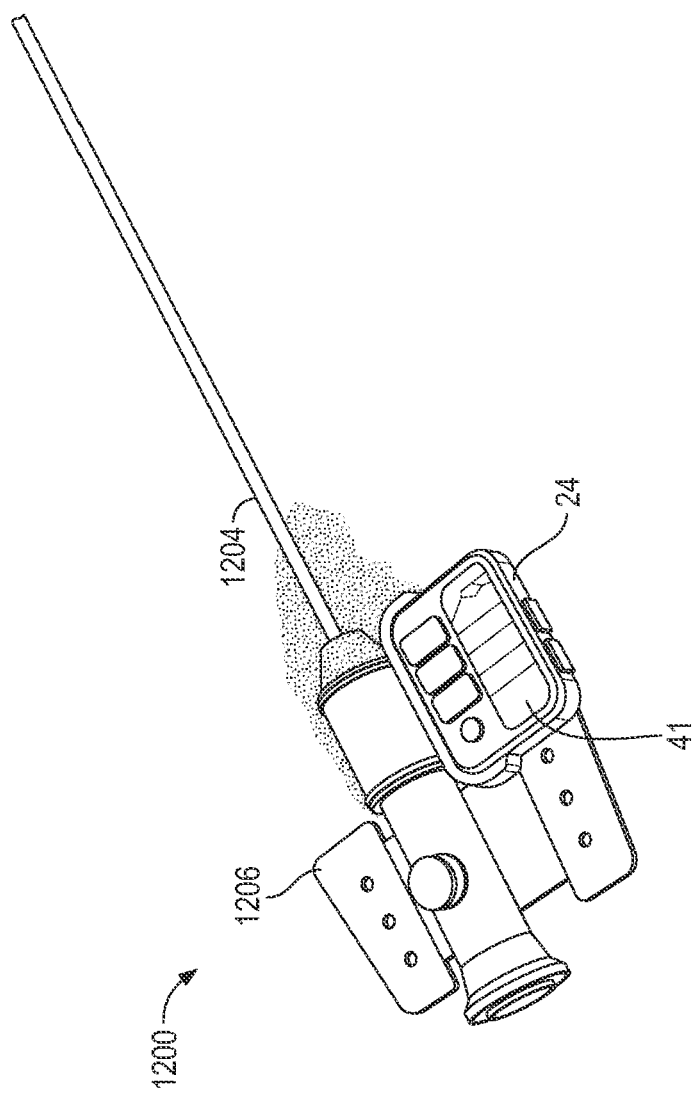

METHOD, SYSTEM, AND DEVICES OF SAFE, ANTIMICROBIAL LIGHT-EMITTING CATHETERS, TUBES, AND INSTRUMENTS

CROSS-REFERENCE TO RELATED APPLICATION

This application is a continuation of earlier filed U.S. patent application Ser. No. 15/832,242 entitled "METHOD, SYSTEM, AND DEVICES OF SAFE, ANTIMICROBIAL LIGHT-EMITTING CATHETERS, TUBE, AND INSTRUMENTS" filed on Dec. 5, 2017, the contents of which are incorporated herein by reference.

BACKGROUND OF THE INVENTION

1. Field of the Invention

The present patent document relates generally to catheters, tubes, and instruments and more particularly to antimicrobial light-emitting catheters, tubes, and instruments that are safe to human tissue.

2. Description of the Related Art

A catheter is a thin tube made from medical grade materials serving a broad range of functions. Catheters are medical devices that can be inserted into various body cavities, ducts, or vessels to treat diseases, provide access for surgical procedures, facilitate drainage of bodily fluids, and allow administration of fluids or gases, among other functions. Through modification of catheter materials or design, it is possible to tailor catheters for vascular, cardiovascular, neurovascular, neurological, renal, urological, oncologic, gastrointestinal, spinal, peripheral intervention, endoscopic, patient-monitoring, surgical, interventional radiology, respiratory, wound management, ophthalmic applications, among others.

The process of inserting a catheter is catheterization. Catheters may be flexible or very stiff, depending upon the intended use.

A catheter left inside the body, either temporarily or permanently, may be referred to as an indwelling catheter (for example, a peripherally inserted central catheter). A permanently inserted catheter may be referred to as a permcath.

Despite the many benefits and necessity of using catheters, use is not without problems, such as the well-documented risk of catheter-related infections.

Regarding urinary catheters (also called Foley catheters), urinary tract infections (UTI) associated with these catheters are the leading cause of secondary health care-associated bacteremia. Approximately 20 percent of hospital-acquired bacteremias arise from the urinary tract, and the mortality associated with this condition is about 10 percent.

Bacteriuria in patients with indwelling bladder catheters occurs at a rate of approximately 3 to 10 percent per day of catheterization. Of those with bacteriuria, approximately 10 to 25 percent develop UTI. The most important risk factor is the duration of catheterization. Other risk factors include errors in catheter care, such as failure to adhere to antiseptic technique.

For intravascular catheters, nosocomial (hospital-acquired) bloodstream infections (BSIs) are an important cause of morbidity and mortality, with an estimated 250,000 cases occurring each year in the United States. Sixty-four percent of the nosocomial BSIs reported were primary BSIs. Most primary BSIs are associated with intravascular catheters, and central venous catheters (CVCs) in particular. Approximately 90 percent of annual catheter-related bloodstream infections in the United States occur with CVCs. Prospective studies have shown that every intravascular device confers a risk of infection to patients, although some (e.g., non-tunneled central venous catheters and pulmonary artery catheters) carry greater risk than others (e.g., peripheral intravenous catheters). For central venous catheters, the site of catheter placement affects the risk of infection, with the subclavian site being associated with less risk than others. Although there is a lower risk of infection, there is a substantially higher risk of pneumonia.

Indwelling catheters are a frequent source of infection in many populations who required long-term venous access, including hemodialysis and oncology patients as well as those receiving total parenteral nutrition. In 2008 in the United States, an estimated 37,000 CR-BSIs occurred among patients receiving outpatient hemodialysis. Similarly, tubes and instruments used in healthcare settings are also prone to colonization by microorganisms, which may, in turn, lead to infection of the exposed patient.

The risk of catheter-associated infection is multifactorial, dependent on host factors (e.g., chronic illness, immune deficiency, loss of skin integrity) and catheter factors (e.g., catheter type, location of catheter, and duration of placement). The sources of infection from a catheter can be attributable to four major sources: colonization from the skin, intraluminal or hub contamination, secondary seeding from a bloodstream infection (extraluminal), and, rarely, contamination of the infusate. Catheter-based approaches to reduce one or more of the sources of infection merit application—in particular, efforts aimed to reduce microorganisms at the skin and catheter tube.

Current strategies for reducing catheter, tubes, and instrument related infections include use of antibiotics and microbial resistant coatings. However, coatings or material modifications do not kill already colonized organisms. Antimicrobial-impregnated catheters, such as with chlorhexidine-silver sulfadiazine, have failed to reduce infection rates. Minocycline-rifampin-coated tubes, instruments and catheters have increased risk of anaphylaxis and emergence of resistant organisms. Experiments with silver-impregnated collagen cuffs have resulted in no bacteremia benefit in trials of tunneled catheters or double or triple lumen catheters. Use of Heparin bonding to reduce thrombosis which may or not be related to infection, have not resulted in specific benefits. Antibiotic locks have increased risk of development of resistant organisms. Further, use of antibiotics, however, is only after the patient has contracted an infection, which is undesirable. The use of antibiotics can cause adverse and systemic effects. Furthermore, the rise of antibiotic resistant strains of bacteria has made treatment of infections more difficult. Antimicrobial coatings for medical devices generally have proven ineffective at preventing infections. Antimicrobial coatings may only be able to prevent or slow bacterial colonization (i.e., bacteriostatic) but are not able to reduce or kill bacteria already colonized on a surface (i.e., bactericidal).

New approaches to combating infection without the use of antibiotics are needed to reduce or slow antibiotic resistance. The rising problem of antibiotic resistance has prompted precautions against creating, and if possible eliminate, multidrug resistance in concert with exploring new methods to kill pathogenic microorganisms. The investigation of novel non-antibiotic approaches, which can prevent and protect against infectious diseases should be prioritized. Promising non-antibiotic approaches include light-based technologies. Advantages of light-based antimicrobial therapies lie in their ability to eradicate microbes regardless of antibiotic resistance, and the fundamental improbability of the microbes themselves developing resistance to these light-based therapies due to the rather non-specific nature of the targets and the dynamic modifiability of various light parameters at the first sign of organism tolerance.

Although promising, not all light-based antimicrobial approaches may be applicable for integration into devices such as catheters, tubes, and instrument applications. For example, specific wavelengths in the ultraviolet spectrum are known to cause harmful effects to human tissue (e.g., cancer) and can degrade many natural and synthetic polymers. As such, these particular wavelengths would preclude safe use in medical devices that are inserted into the patient. Therefore, certain light-based antimicrobial approaches may be applicable for integration into catheter, tube, and instrument applications to reduce associated infections.

Accordingly, there is a need in the art for patient-safe, non-antibiotic, germicidal catheters, tubes, and instruments that kill microorganisms on their surfaces to reduce the risk of infection.

SUMMARY OF THE INVENTION

The light-emitting antimicrobial catheter solves the problems noted in the prior art by providing a catheter that includes a thin, flexible tube having an optically transparent wall; and a light transmitter configured and arranged to emit light through the tube, which may be ultraviolet C (UVC) irradiation, photodynamic therapy (PDT), violet-blue light therapy, and other light-based therapies. In one embodiment, violet-blue wavelengths (from 400-500 nm) of visible spectrum light that have both antimicrobial effects and are safe to expose to human tissue, such as 405 nm or 415 nm in wavelength, may be used. A patient is catheterized with the catheter and a prophylactic or therapeutic amount of light is administered to the patient, thereby reducing the risk of infections introduced from the catheter itself, or received through the opening in the body that receives the catheter. The antimicrobial light targets sources of infection, in particular at the skin interface and the tube (intraluminal and outer surface). The catheter may be configured for use in any application, including the urinary tract, intravascular, ventricular drains, neuro catheters, epidural catheters, suction catheters, rectal tubes, or any other catheter, tube, and tube-like instruments that may be indwelling or temporary in placement. Light may be administered for any duration sufficient to kill pathogens. Additionally, the emitted light may be pulsed, varied in intensity, applied when or before the catheter device is inserted or used. The variables of intensity, duration, and wavelength may be adjusted as needed or necessary to achieve the maximum antimicrobial or therapeutic effect while minimizing any side effects to the patient. Furthermore, visible spectrum violet-blue light (e.g., 405 nm and 415 nm wavelength) is considered safe to mammalian cells thereby making both safe to the patient and therapeutic in its germicidal efficacy. Although the mechanism of the antimicrobial effect of visible spectrum violet-blue light is still not fully understood, the commonly accepted hypothesis is that violet-blue light excites endogenous intracellular porphyrins, and this photon absorption then leads to energy transfer and ultimately, the production of highly cytotoxic reactive oxygen species. The biocidal effect of violet-blue light represents a photodynamic inactivation mechanism that involves the absorption of photons in the region of 405 nm by endogenous porphyrin molecules within microbial cells. This absorption initiates excitation of the porphyrin molecules, and excited porphyrins interact with oxygen or cell components to produce reactive oxygen species (ROS) causing oxidative damage and microbial cell death. Cell death has been accredited to oxidative damage to the cell membrane; however, it is likely that, due to the non-selective nature of ROS, multi-target damage will be induced in exposed microbial cells.

For instance, by way of example and not limitation, some pathogens found to be susceptible to violet-blue antimicrobial visible spectrum light include bacteria, yeast, fungi, spores, and viruses, such as *Clostridium difficile, Clostridium perfringens, Enterococcus, Listeria*, Methicillin-resistant *Staphylococcus aureus* (MRSA), *Propionibacterium acnes, Salmonella enteritidis, Staphylococcus aureus, Staphylococcus epidermidis, Streptococcus mutans, Streptococcus pyogenes*, other Streptococci species, Vancomycin-resistant *Enterococcus, Streptomyces* phage φC31, *Bacillus cereus, Bacillus megaterium, Bacillus subtilis, Acinetobacter baumannii, Campylobacter jejuni, Escherichia coli, Fusobacterium nucleatum, Helicobacter pylori, Klebsiella pneumoniae, Mycobacterium, Porphyromonas gingivalis, Prevotella intermedia, Prevotella melaninogenica, Prevotella nigrescens, Proteus vulgaris, Pseudomonas aeruginosa, Shigella sonnei, Aspergillus niger, Candida albicans, Saccharomyces cerevisiae, Enterobacter*, and *Serratia*, among others

BRIEF DESCRIPTION OF THE DRAWINGS

These and other features, aspects, and advantages of the present invention will become better understood with reference to the following description, appended claims, and accompanying drawings where:

FIG. 3E is a cross-sectional view with a fourth embodiment with an add-on sleeve on the catheter tube;

FIG. 4 is a flow chart of a method of treatment using the antimicrobial catheter as disclose herein;

FIG. 6A is a partial perspective view of an exemplary embodiment of a long-term hemodialysis catheter made in accordance with the present invention;

FIG. 6D is a perspective view illustrating use on a patient of a long-term hemodialysis catheter having an integral light emitter made in accordance with the present invention;

FIG. 12A is a partial perspective view of an exemplary embodiment of a peripheral intravenous catheter made in accordance with the present invention;

DETAILED DESCRIPTION OF THE INVENTION

As will be described in greater detail below, the light-emitting, antimicrobial instruments, tubes, and catheters includes a thin, flexible tube having an optically transparent wall; and a light transmitter configured and arranged to emit light through the tube and/or other portions of the instrument, which may be ultraviolet C (UVC) irradiation, photodynamic therapy (PDT), violet-blue light therapy, and other light-based therapies. In one embodiment, antimicrobial light that is safe to expose to human tissue, visible spectrum violet-blue light from 400-500 nm in wavelength, such as 405 nm or 415 nm, for instance, may be used. The instrument, tube, or catheter is used on a patient and a therapeutic amount of light is administered to kill any microbes on the surface of the instrument, tube, or catheter, thereby reducing the risk of infection to the patient. The instrument, tube, or catheter may be configured for use in cardiovascular, neurovascular, neurological, renal, urological, oncologic, gastrointestinal, spinal, peripheral intervention, endoscopic, patient-monitoring, surgical, interventional radiology, respiratory, wound management, ophthalmic or any other health application, and may be indwelling or temporary. Light may be administered for the duration of use or another time period, such as 5, 10, 15, 30 or 60 minutes, for instance. Because the antimicrobial properties of visible spectrum violet-blue light, the risk of bacterial infection through the use of the instrument, tube, or catheter is reduced.

Figure 1A:
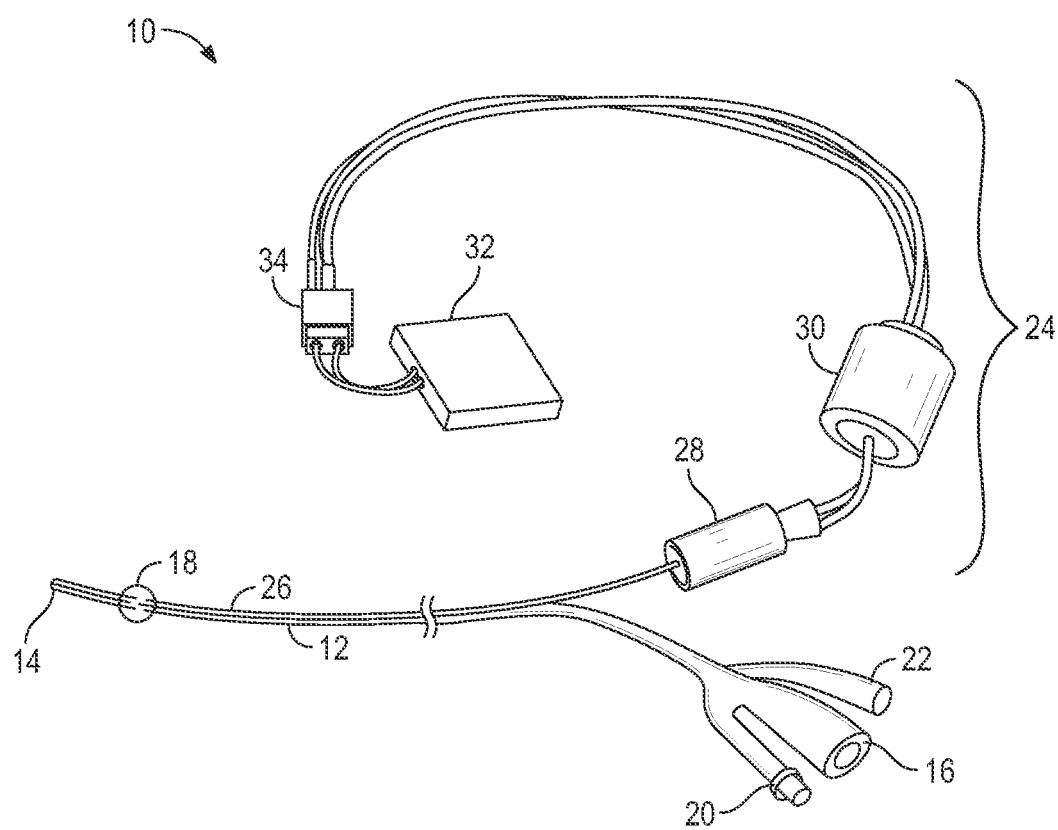
FIG. 1A is a perspective view of a first embodiment of an antimicrobial light-emitting catheter configured for urinary tract use.

Referring to FIG. 1A a first embodiment of a light-emitting antimicrobial catheter for use in the urinary tract is illustrated generally at 10. The catheter 10 includes an optically transparent tube 12 with a tip 14 and a drain 16. The catheter 10 may include an inflatable balloon 18 near the tip 14. An inflation port 20 is provided to inflate the balloon 18. In some configurations, the catheter 10 may include an irrigation port 22 as well. A light transmitter 24 is connected to the tube 12 and configured to emit light through the optically transparent wall of the catheter 10. The light transmitter 24 may include a side-emitting optical fiber 26 connected to a light source 28, a control circuit 30 to control the light source 28, and a power source 32, to power the light source 28 and control circuit 30. In some embodiments, the drain 16, inflation port 20, and/or irrigation port 22 may also be made from optically transparent material to transmit light to the patient's skin underlying the catheter 10.

Figure 1B:
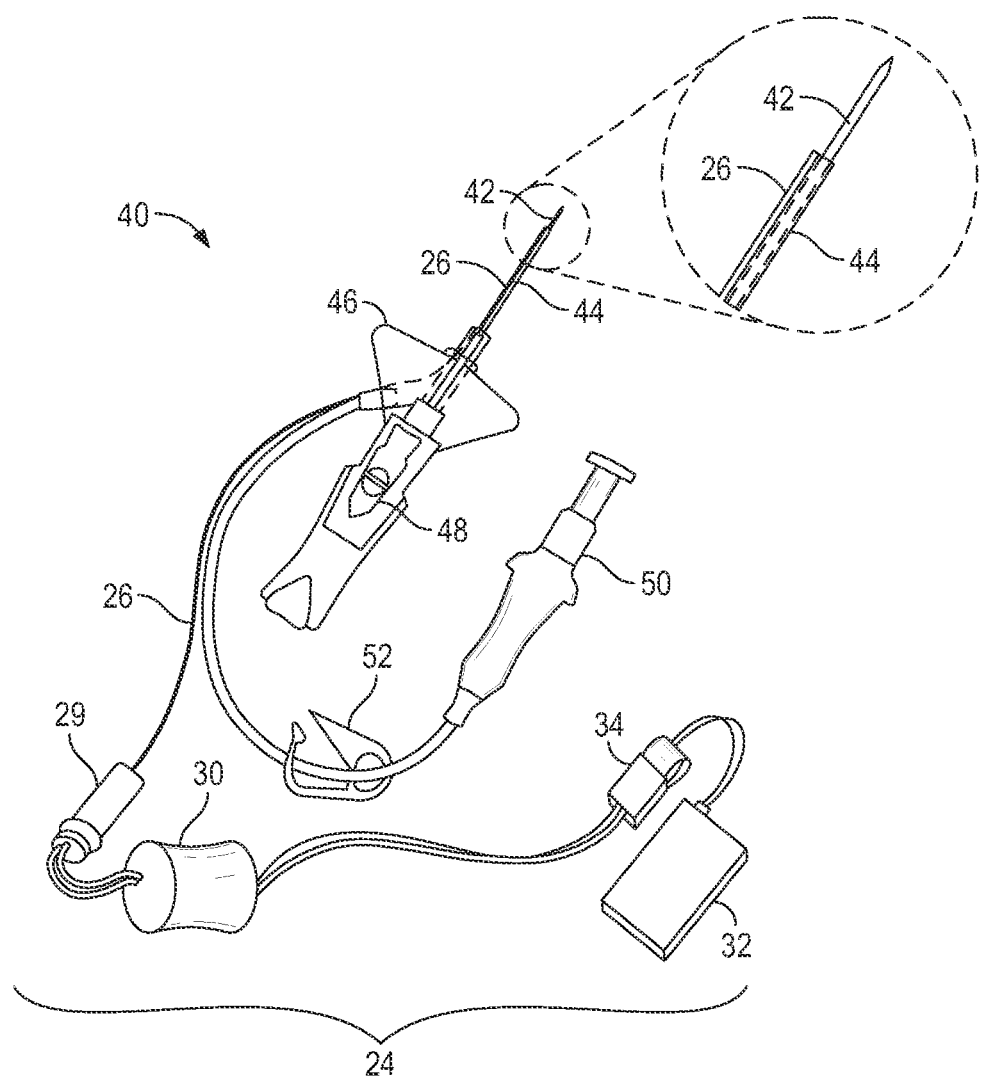
FIG. 1B is a perspective view of a second embodiment of an antimicrobial light emitting catheter configured for intravascular use.

Referring to FIG. 1B a second embodiment of a light-emitting antimicrobial catheter for intravascular use is illustrated generally at 40. In particular, a peripheral venous catheter is shown. The catheter 40 includes a tip 42 for insertion into a vein of the patient and delivery of a cannula 44 into the vein and wings 46 for handling and securing the catheter 40 with adhesive to the patient's body. The cannula 44 is an optically transparent tube for delivery for fluids and medication into the vein. The exterior portion of the body of the catheter 40, including wings 46, may be optically transparent plastic as well, for delivery of light from the light emitter to the skin of the patient underlying the catheter 40. The tip 42 is partially withdrawn after insertion of the cannula 44, leaving the cannula 44 within the vein. A valve 48 may be provided for delivery of medication by syringe to the patient. A port 50 may be included for connection of an infusion line to the catheter 40. A clamp 52 may be included to shut off the catheter 40, for example, during change of intravenous fluid drip. A light transmitter 24 is connected to the cannula 44 and configured to emit light through the optically transparent wall. The light transmitter 24 may include a side-emitting optical fiber 26, connected to a light source 28, a control circuit 30 to control the light source 28 and a power source 32, to power the light source 28 and control circuit 30.

Figure 1C:
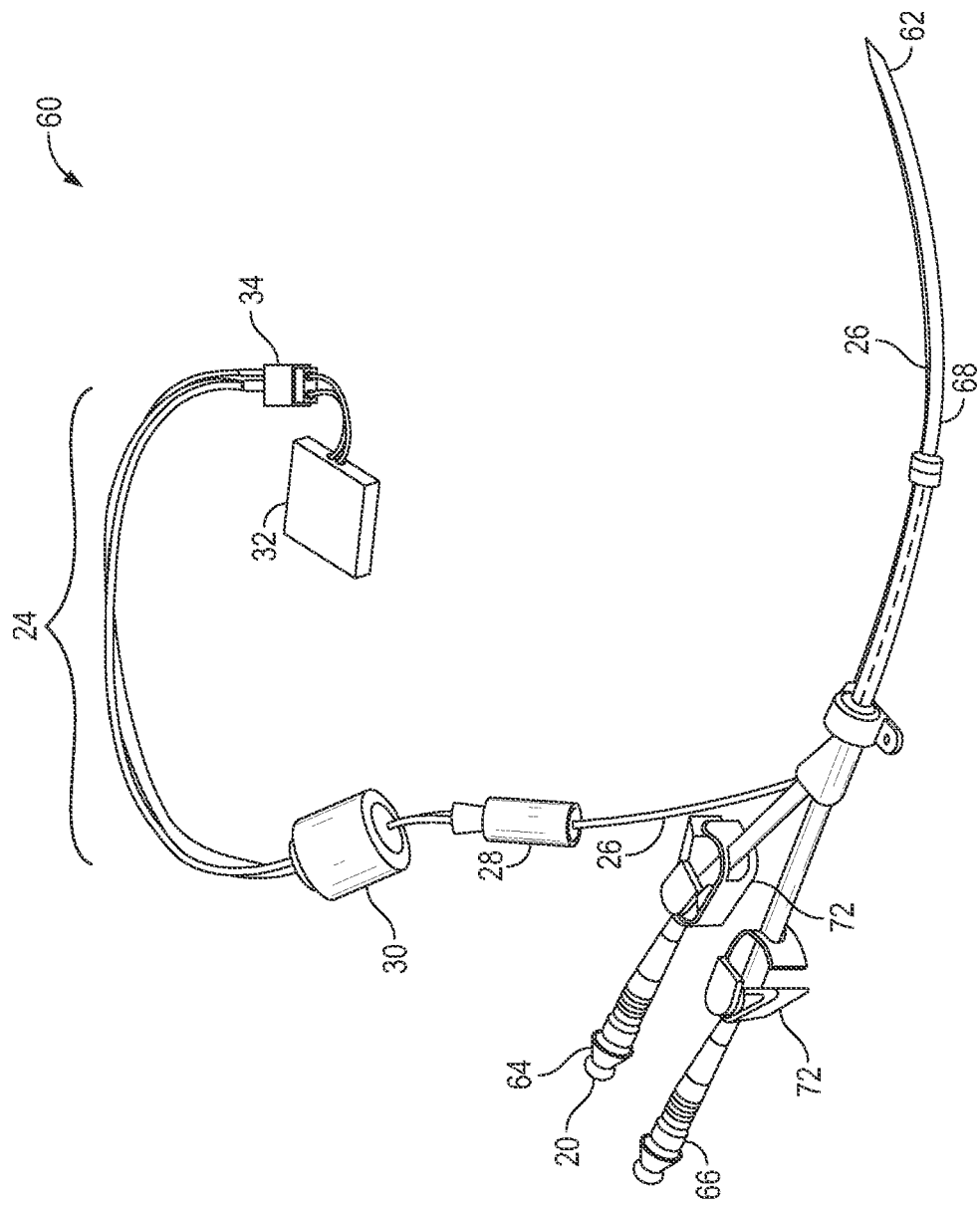
FIG. 1C is a perspective view of a third embodiment of an antimicrobial light emitting catheter configured for intravascular use.

Referring to FIG. 1C, a third embodiment of a light-emitting antimicrobial catheter for intravascular use is illustrated generally at 60. In particular, a hemodialysis catheter is shown. The catheter 60 includes a tip 42 for insertion into a vein of the patient. The catheter 60 includes a cannula 68 which includes a venous lumen 64 and an arterial lumen 66, for drawing away and returning blood, respectively, to the patient. The lumens 64, 66 and cannula may be formed from an optically transparent material. Each lumen may include its own port 70. Each lumen may also include a clamp 72 to shut off the respective lumen 64, 66. A light transmitter 24 is connected to the lumen 64, 66 and/or cannula 68 and configured to emit light through the optically transparent material. The light transmitter 24 may include a side-emitting optical fiber 26, connected to a light source 28, a control circuit 30 to control the light source 28 and a power source 32, to power the light source 28 and control circuit 30.

Figure 2:
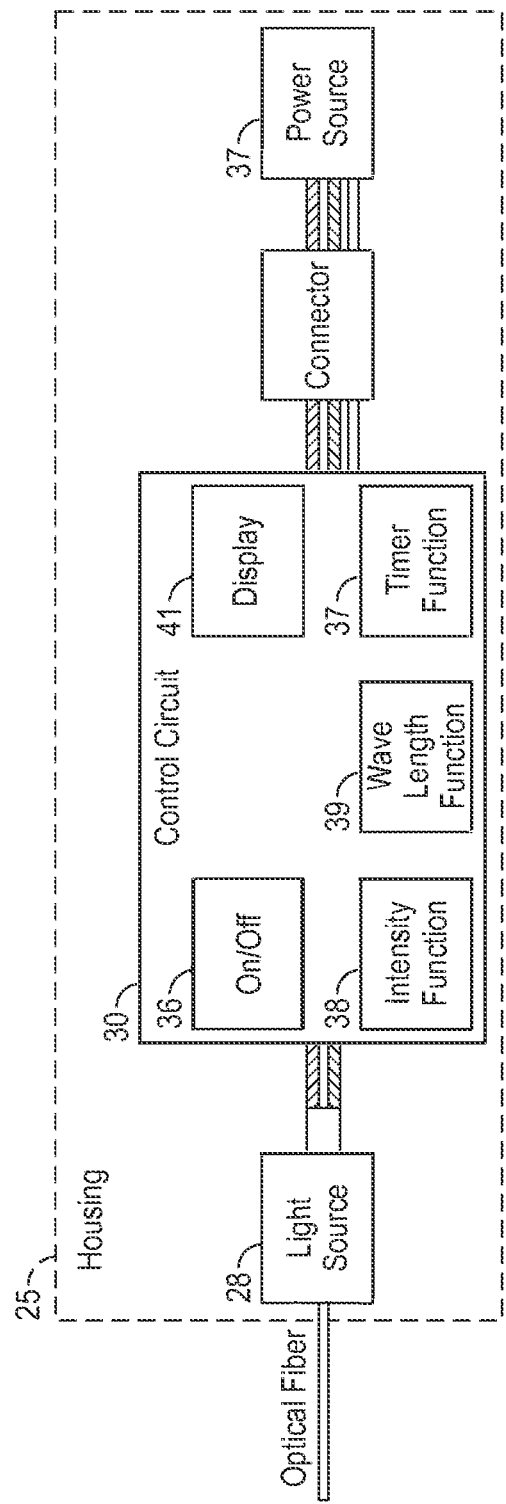
FIG. 2 is a block diagram of light transmitter.

Referring to FIG. 2, an illustration of an embodiment of a light transmitter 24 is shown generally. The light transmitter 24, as noted above, includes a light source 28, such as an LED laser module that may be optically connected to an optical fiber monofilament 26. The light source 28 is electrically connected to a control circuit 30 to control the functioning of the light source 28, which will be further described below. Extending from the control circuit 30 is an optional connector 34 electrically connected to the control circuit 32, for connecting to a power source 32, such as a battery or DC power supply. The optional connector 34 allows a power source 32 to be easily changed; for instance, a fresh battery provided. The light source 28 may be configured to emit light in antimicrobial light wavelengths. In one embodiment, the light source 28 is configured to emit light in a wavelength of 405 nm or 415 nm. The light source may be configured to emit any wavelength of light, which have been shown to have antimicrobial properties without the adverse risks associated with certain electromagnetic radiation wavelengths. The light transmitter may include an optional housing 25 to enclose and protect the components of the light transmitter 24.

In some embodiments, the control circuit 30 may provide additional functionality besides mere power management and an ON/OFF control 36 for the light source 28. For instance, the control circuit 30 may include a timer function 37 for automatic shutoff after a preselected amount of time, such as 5, 10, 15, 30 or 60 minutes or longer. Alternatively, or in addition to, the preselected amount of time may be user settable to any desired time period. The control circuit 30 may also include an intensity function 38 to control the brightness or intensity of the emitted light from the light source 28. In some embodiments, the control circuit 30 may also include a wavelength function 39 to select the wavelength of emitted light to a desired wavelength form the light source 28. In some embodiments, the control circuit 30 may include a function to pulse the light source 28 at predetermined intervals and/or patterns. In some embodiments, the control circuit 30 may include a display 41 to show information regarding the timer, intensity and/or wavelength. The control circuit 30 may be integrated with the light source 28.

Referring to FIGS. 3A-3D, the light transmitter 24 may be connected to the optically transparent tube or cannula of the catheter in a variety of configurations, described in greater detail below. As mentioned above, the light transmitter may include a side-emitting optical fiber 26, which may be a monofilament. These images are not to scale, but illustrated to accentuate the respective structures for better understanding.

Figure 3A:
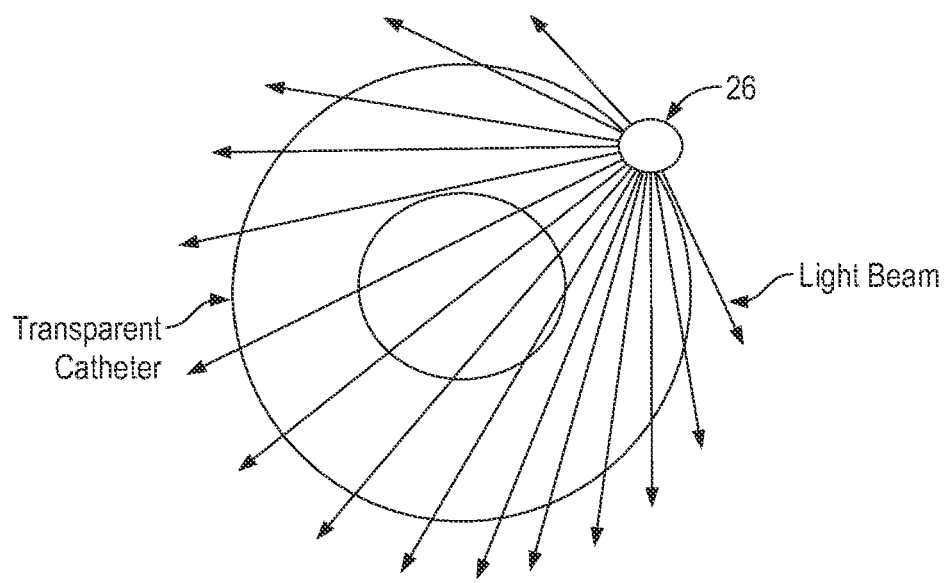
FIG. 3A is a cross-sectional view of a first embodiment of a side embedded light transmitter on the catheter tube.

Referring to FIG. 3A, a cross-sectional view of a first embodiment where an optical fiber 26 is embedded on the wall of the catheter tube 12. In this configuration, the optical fiber 26 is integrally formed with the catheter tube 12, 44 such that light emitted from the optical fiber 26 transmits through the catheter tube 12, 44.

Figure 3B:
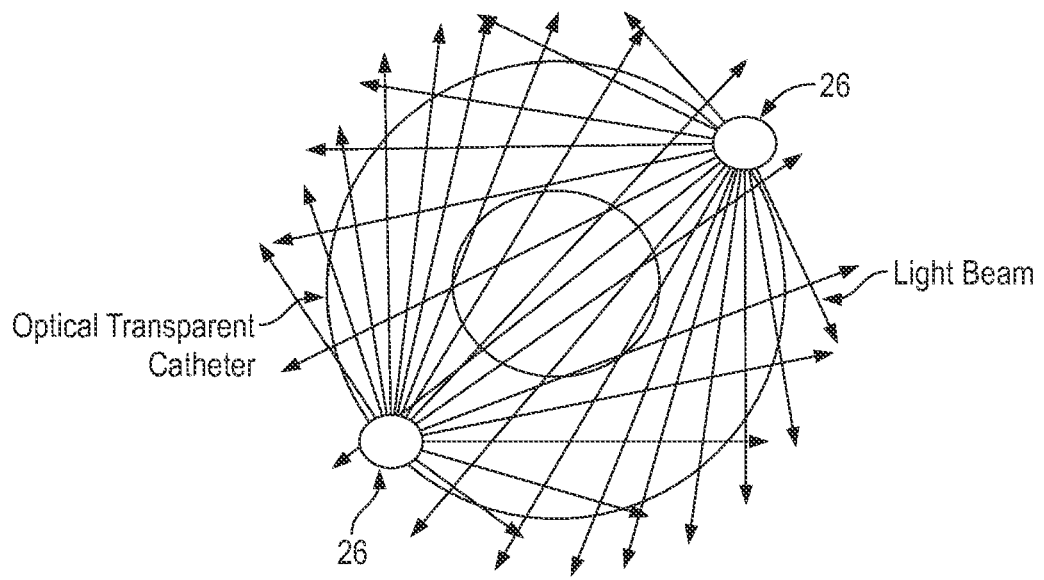
FIG. 3B is a cross-sectional view of a second embodiment with multiple side embedded light transmitters on the catheter tube.

Referring to FIG. 3B, a cross-sectional view of a second embodiment with multiple side embedded optical fibers 26 on the catheter tube 12, 44. In particular, two or more fiber optic monofilaments 26 may be integrally formed in the catheter tube 12, 44, thus ensuring uniform exposure of light from the light source 28 from all directions.

Figure 3C:
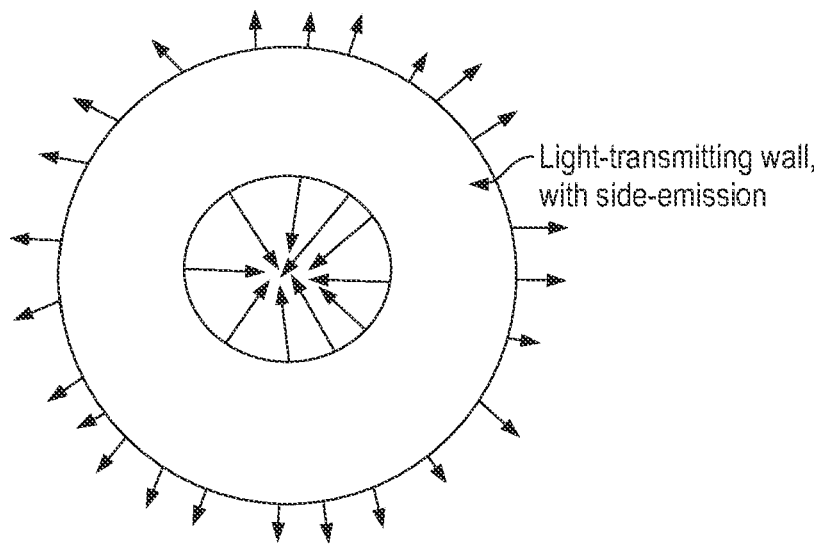
FIG. 3C is a cross-sectional view of a third embodiment with a wall emitter.

Referring to FIG. 3C, a cross-sectional view of a third embodiment with a wall emitter, where the light source 28 is optically connected to the catheter tube and configured to emit light directly through the catheter tube 12, 44 without need for a separate waveguide, such as an optical fiber.

Figure 3D:
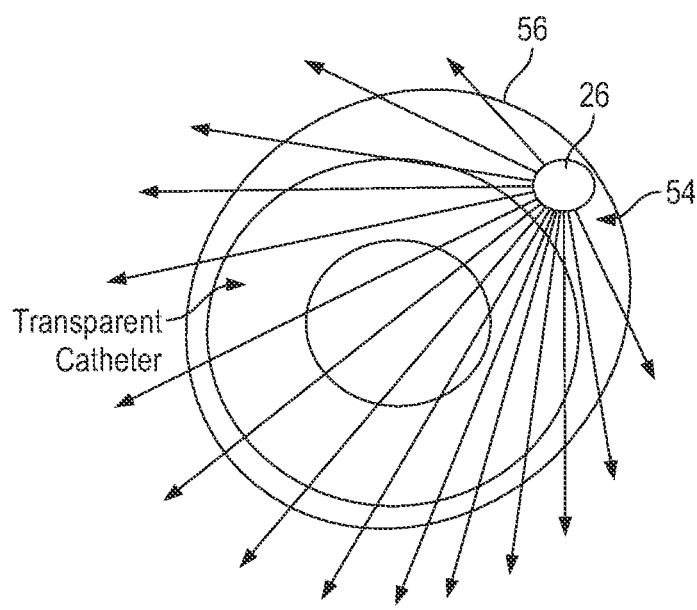
FIG. 3D is a cross-sectional view with a fourth embodiment with an add-on sleeve on the catheter tube.

Referring to FIG. 3D, a cross-sectional view of a fourth embodiment where an optical fiber 26 is embedded within the wall of the catheter tube 12. In this configuration, the optical fiber 26 is integrally formed with the catheter tube 12, 44 such that light emitted from the optical fiber 26 transmits through the catheter tube 12, 44.

The fiber optic 26 may be a plastic optical fiber or polymer optical fiber, such as PMMA (acrylic) and/or polystyrene. The fiber optic 26 may also be made from glass, such as silica, fluorozirconate, fluoroaluminate, outher fluoride glasses, chalcogenide glass, phosphate glass, and sapphire. Optical fiber produced by Corning, such as Corning's Fibrance® light-diffusing fiber may be used. electroluminescent wire (a copper wire coated with phosphor) may also be used as fiber optic 26. Other light transmitting fiber may be used, provided they are safe for the patient, adaptable for catheter, tubes and instruments inserted into the body, and capable of delivery adequate antimicrobial light.

Referring to FIG. 3E, a cross-sectional view with a fourth embodiment with an add-on sleeve 54 on the catheter tube 12,44. In the fourth embodiment, the sleeve 54 may be used as an add-on or retrofit to add light emitting functionality to prior art catheters. Such retrofitted catheters need not be optically clear; the add-on sleeve encircles the tube to coat the surface of the tube with bactericidal light. In this embodiment, the sleeve 54 is a tubular or condom-like sheath structure with a resilient wall that is optically transparent and capable of side-emitting light. A side-emitting optical fiber monofilament 26 is embedded in the wall of the sleeve 54 and configured to emit light through the sleeve 54. The portion of the wall 56 that the optical fiber monofilament 26 is embedded may be thickened to encase the optical fiber 26.

Figure 3F:
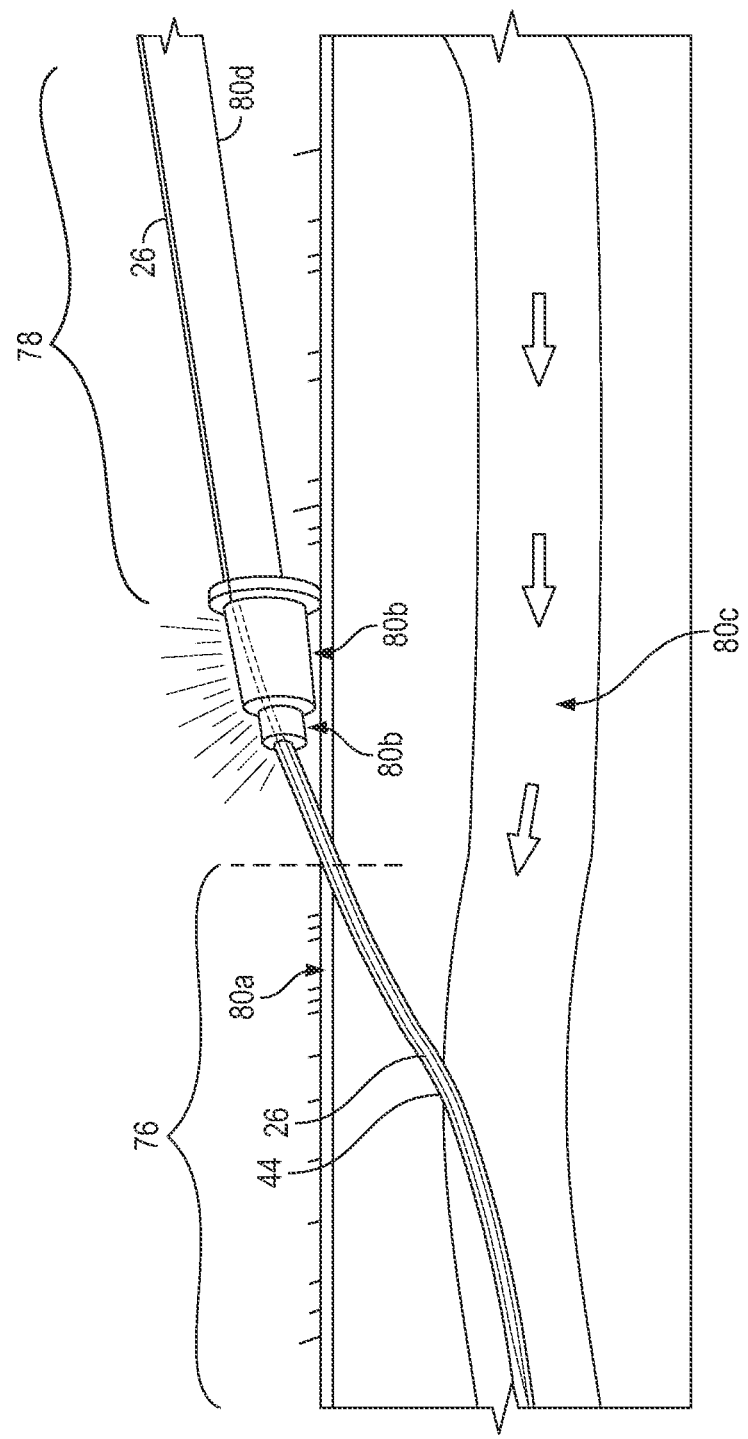
FIG. 3F is a partial cross-section view illustrating use of an intravascular catheter inserted in a patient.

Referring to FIG. 3E, in some embodiments, the catheter may include an interior portion 76, which is placed inside the patient's body, and an exterior portion 78, which is placed on an exterior portion of the patient's body. The light emitter may include a fiber monofilament 26 that is configured to emit light through the cannula 44 on the interior portion 76 of the catheter and also through the exterior portion 78 of the catheter and, consequently, onto the skin of patient. The light emitted onto the skin of the patient reduces the risk of infection on the skin at or nor the site of the catherization, as in FIG. 3F. The risk of catheter-associated infection is multifactorial, dependent on host factors (e.g., chronic illness, immune deficiency, loss of skin integrity) and catheter factors (e.g., catheter type, location of catheter, and duration of placement). The sources of infection from a catheter can be attributable to four major sources: 1) colonization from the skin 80*a*, 2) intraluminal or hub contamination 80*b*, 3) secondary seeding from a bloodstream infection (extraluminal) 80*c*, and, rarely, 4) contamination of the infusate 80*d*. Catheter-based efforts to reduce one or more of the sources of infection merit application.

Referring to FIG. 4, a flowchart illustrating a method of treatment is shown generally at 100. In a first step 102, a catheter with a tube having an optically transparent wall and a light transmitter configured to emit light through the tube is providence. In a second step 104, a patient is catheterized with the catheter. In a third step 106, a therapeutic amount of light is administered with the light transmitter to the patient. The duration of exposure of light could be for the duration the catheter is inserted for the procedure in question or for other time periods, such as five minutes, ten minutes, thirty minutes, one hour or longer. An optional fourth step may include removal of the catheter from the patient. The method may include a step of adjusting a parameter of the light emitter, including adjusting intensity, radiant exposure, dwell time, wavelength, and pulse frequency of the light emitter.

It should be understood that the light-emitting antimicrobial catheter described herein may be used in any number of catheters, tubes, instruments, drains, ports, and devices, such as, arterial lines, balloon catheters, central venous catheters, dialysis catheters, embryo transfer catheter, Electrophysiology study, Fogarty embolectomy catheter, Foley catheters, Groshong line, Hickman line, insulin port, intrauterine pressure catheter, Murphy drip, peripheral venous catheter, peripherally inserted central catheter, peripheral catheters, pulmonary artery catheter, Quinton catheter, Swan-Ganz catheters, Stadium buddy, Suprapubic cystostomy, umbilical line catheters, midline catheters, ureteric balloon catheter, bowel management systems, gastric management systems, cardiac monitoring, intra-abdominal pressure monitoring systems, pacing electrodes, medical tubing, hemodialysis catheters, catheter repair systems, inflation devices, temperature-sensing systems, angioplasty, balloon PTA catheters, nontunneled central catheters, tunneled central catheters, peripherally inserted central catheters, implantable ports, Broviac catheter, Groshong line, Huber needle, balloon dilation catheters, carotid shunts, tunnelers, central venous catheter replacement connectors, introducers, micro introducers, recanalization catheters, guidewires, chronic total occlusion systems, enteral feeding systems, gastrostomy devices, percutaneous endoscopic gastrostomy feeding device, jejunal feeding devices, Seldinger needles, puncture needles, gastric decompression tube, stoma measuring systems, left ventricular assist device driveline, hemodialysis catheters, intraperitoneal dialysis catheters, ports, implantable ports, dual lumen ports, peritoneal ports, procedural devices, stent grafts, support catheters, channel drains, round drains, flat drains, gravity drains, PVC drains, sump drains, passive drains, active drains, crossing support catheters, surgical grafts, grafts, tip confirmation systems, valvuloplasty systems, valvuloplasty catheters, intracranial catheters, epidural catheters, subcutaneous administration, valvuloplasty perfusion catheters, vascular probes, vena cava filters, vena cava filter retrieval systems, vascular stents, biliary stents, subarachnoid space catheters, expandable biliary stents, endovascular stent graft, grafts, vascular stents, revision grafts, vascular access grafts, vascular grafts, bypass grafts, biopsy systems, breast biopsy systems, biopsy probes, biopsy tubing, ultra sound procedure systems, stereotactic procedure systems, MRI procedures systems, CT procedure systems, drivers, probes, introducers, vacuum-assisted procedure systems, coaxial cannulas, tissue marker systems, localization systems, localization devices, localization wires, needles, guide wires, sheaths, catheters, cannulas, core biopsy instruments, needles, coaxial biopsy needles, drainage catheters, aspiration needles, biopsy needles, PTFE products, breast localization wire, breast tissue markers, laparoscopic instruments, access needles, needles, obturators, guide wires, radial approach accessories, sheath introducers, angiography systems, diagnostic cardiology catheters, diagnostic guide wires, fluid management systems, nephrostomy tube, drains, venous catheter, balloon septostomy, balloon angioplasty, tubing, fluid administration systems, high pressure tubing, pressure monitoring tubing, guidewire accessories, manifolds, stopcocks, adapters, syringes, transducers, aspiration catheters, guiding catheters, hemostasis valves, hemostasis accessories, inflation devices, pericardiocentesis catheters, steerable microcatheters, stent positioning system, compression devices, cardiac rhythm management devices, introducers, electrophysiology devices, pressure monitoring devices, infection control solutions, pens, safety management devices, waste management devices, transradial access, adapters, introducers, dilators, needles, peritoneal dialysis devices, peritoneal dialysis catheters, hemodialysis instruments, hemodialysis devices, hemodialysis catheters, chronic dialysis catheters, tunneled dialysis catheter, curved needles, catheter extractors, hemodialysis access graft, inside-out access catheters, diagnostic guide wires, diagnostic peripheral catheters, angiography devices, fluid management devices, tubing, medical tubing, non-medical tubing, guide wire accessories, hydrophilic guide wires, syringes, balloon catheters, inflation devices, snares, support catheters, therapeutic infusion systems, infusion pumps, infusion pump accessories, infusion pump tubing, fluid dispensing systems, infusion catheters, drainage systems, valve adapters, drainage tubing, connecting tubes, drainage catheters, paracentesis systems, paracentesis devices, thoracentesis devices, thoracentesis systems, hemostasis devices, hemostasis instruments, hemostasis systems, valves, connectors, adaptors, syringes, bags, waste bags, embolotherapy instruments, tumor ablation systems, vertebral compression fracture systems, vertebral augmentation system, vertebroplasty, straight balloons, steerable balloons, steerable needles, access instruments, bone cement systems, percutaneous instruments, percutaneous access, percutaneous drainage, retrieval devices, ureteral catheters, straight catheters, pigtailed catheters, cobra-shaped catheters, Shepherd catheters, hydrophobic catheters, intermittent catheters, pediatric catheters, Judkins left catheters, Judkins right catheters, Judkins left short tip catheters, Judkins right short tip catheters, Amplatz left catheters, Amplatz right catheters, left coronary bypass catheters, right coronary bypass catheters, cardiac pigtail catheters, multipurpose catheters, diagnostic catheters, angiography catheters, guiding catheters, angioplasty catheters, balloon catheters, PTCA wire, butterfly catheters, ureteral stents, stents, kidney stone management system accessories, patient-monitoring systems, patient-monitoring cables, patient-monitoring accessories, tumor ablation systems, image-guided procedures, external catheters, external catheter accessories, endotracheal tubes, Jackson-Pratt drain, Blake drain, Penrose drain, negative pressure wound therapy drains, redivac drain, pigtail drain, Davol drain, chest tube, wound manager, surgical drains, rubber drain, Kehr's t-tube, trocars, close wound drainage systems, open wound drainage systems, extruded tubing, polyimide tubing, heat shrink tubing, reinforced tubing, PTFE liner tubing, balloon catheters, reinforced shaft catheters, open suction catheter systems, nasogastric tubes, wound drains, wound evacuators, skin care, wound care, irrigation systems, Foley catheter stabilization, intermittent catheters, special Foley catheters, Foley catheters, urinary incontinence systems, kidney stone laser fibers, kidney stone access sheaths, kidney stone dilation systems, guidewires, steerable guidewires, reshapable guide wires, microcatheters, steerable microcatheters, intraventricular catheters, tracheobronchial stents, delivery systems, over-the-wire visualization systems, direct visualization systems, pulmonary balloon dilator, sizing devices, stent sizing device, brochoalveolar lavage instruments, endoscopic instruments, endoscopic devices, endoscopic accessories, retrieval devices, esophageal stent, cholangiography devices, balloon dilators, probes, negative pressure syringes, sizing devices, inflation devices, irrigation devices, surgical instruments, procedural instruments, endoscopic devices, laparoscopic devices, minimally invasive surgery instruments, suction devices, urinary catheterization, and intraperitoneal catheters, endotracheal tubes, ventilator tubing, gastrostomy tubes, nasogastric tubes, Levin tube, SUMP or SALEM tubes, Moss tube, Sengstaken-Blakemore tubes, Minnesota tube, Nutrifl ex tube, orogastric tubes, surgical tubes, medical tubes, drainage tubes placed for drainage of fluids/pus/gases, cannulas, among others.

For instance, FIGS. 5A through 12C illustrate various embodiment of other catheters and fluid delivery systems for patients.

Figure 5A:
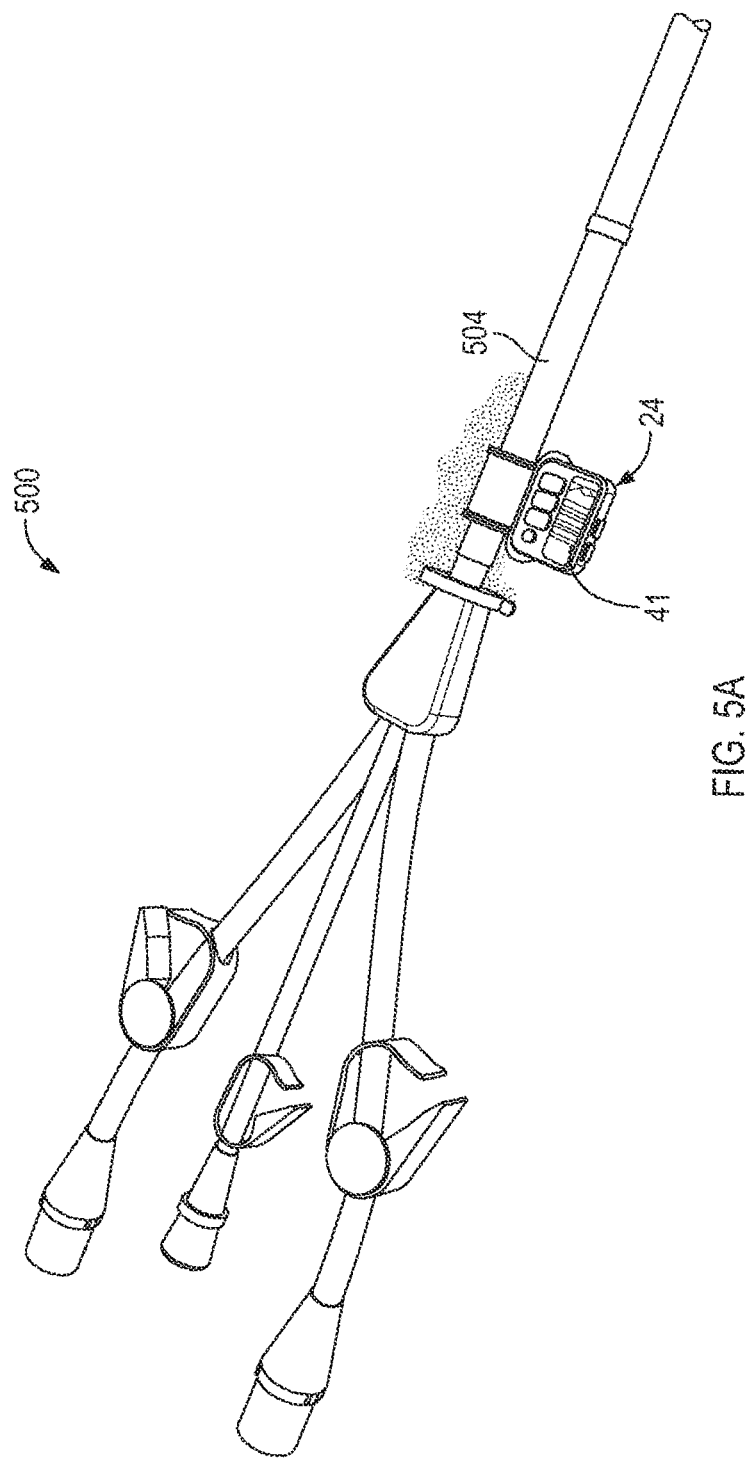
FIG. 5A is a partial perspective view of an exemplary embodiment of a central venous catheter made in accordance with the present invention.

Referring to FIG. 5A, an exemplary embodiment of a central venous catheter made in accordance with the present invention is illustrated generally at 500. The catheter 500 includes a wall 504 comprising an optically transparent material and a light emitter 24 configured to emit light through the wall 504. The light emitter 24 may include a display 41 for viewing the function settings 37, 38, 39 of the control circuit 30 of the light emitter 24.

Figure 5B:
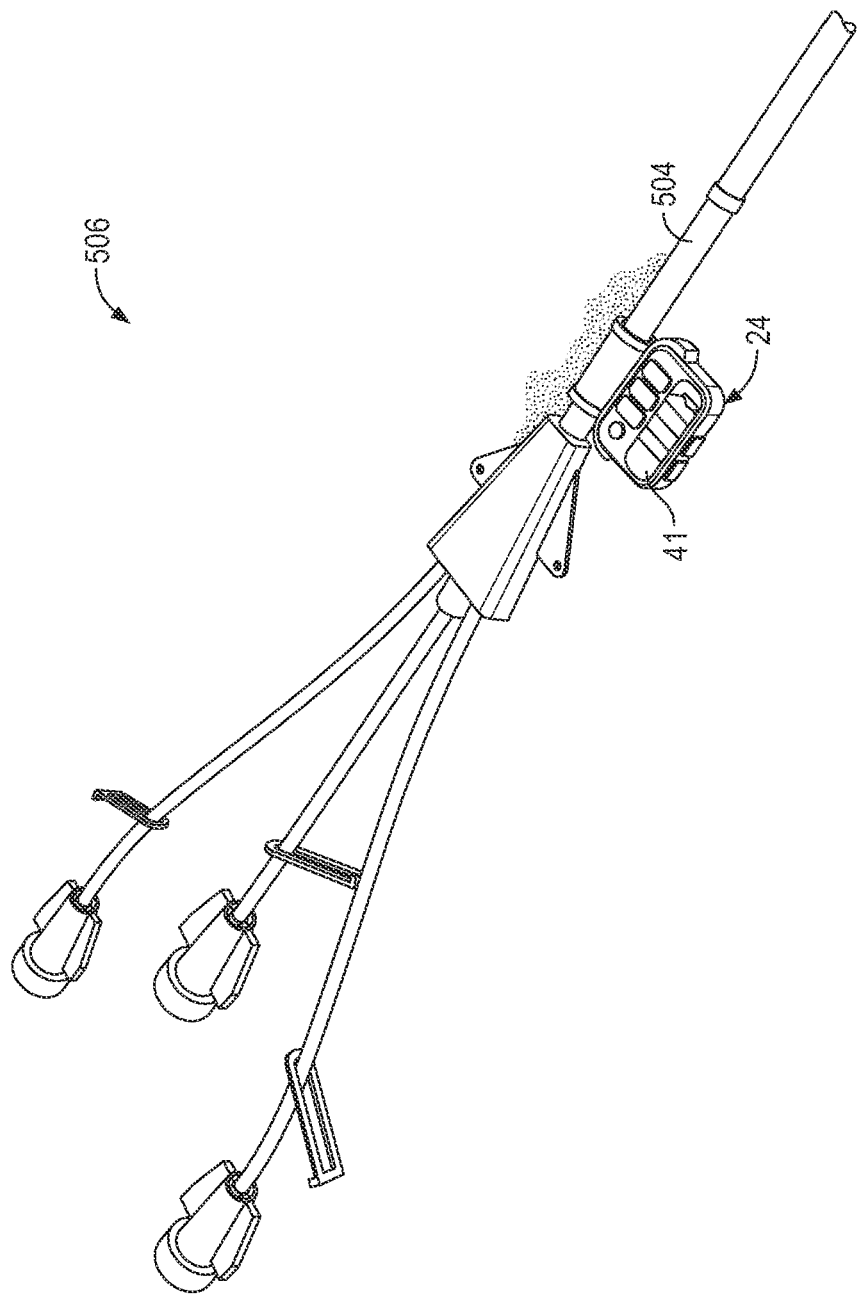
FIG. 5B is a partial perspective view of another exemplary embodiment of a central venous catheter made in accordance with the present invention.

Referring to FIG. 5B, another exemplary embodiment of a central venous catheter made in accordance with the present invention is illustrated generally at 506. The catheter 500 includes a wall 504 comprising an optically transparent material and a light emitter 24 configured to emit light through the wall 504. The light emitter 24 may include a display 41 for viewing the function settings 37, 38, 39 of the control circuit 30 of the light emitter 24.

Figure 5C:
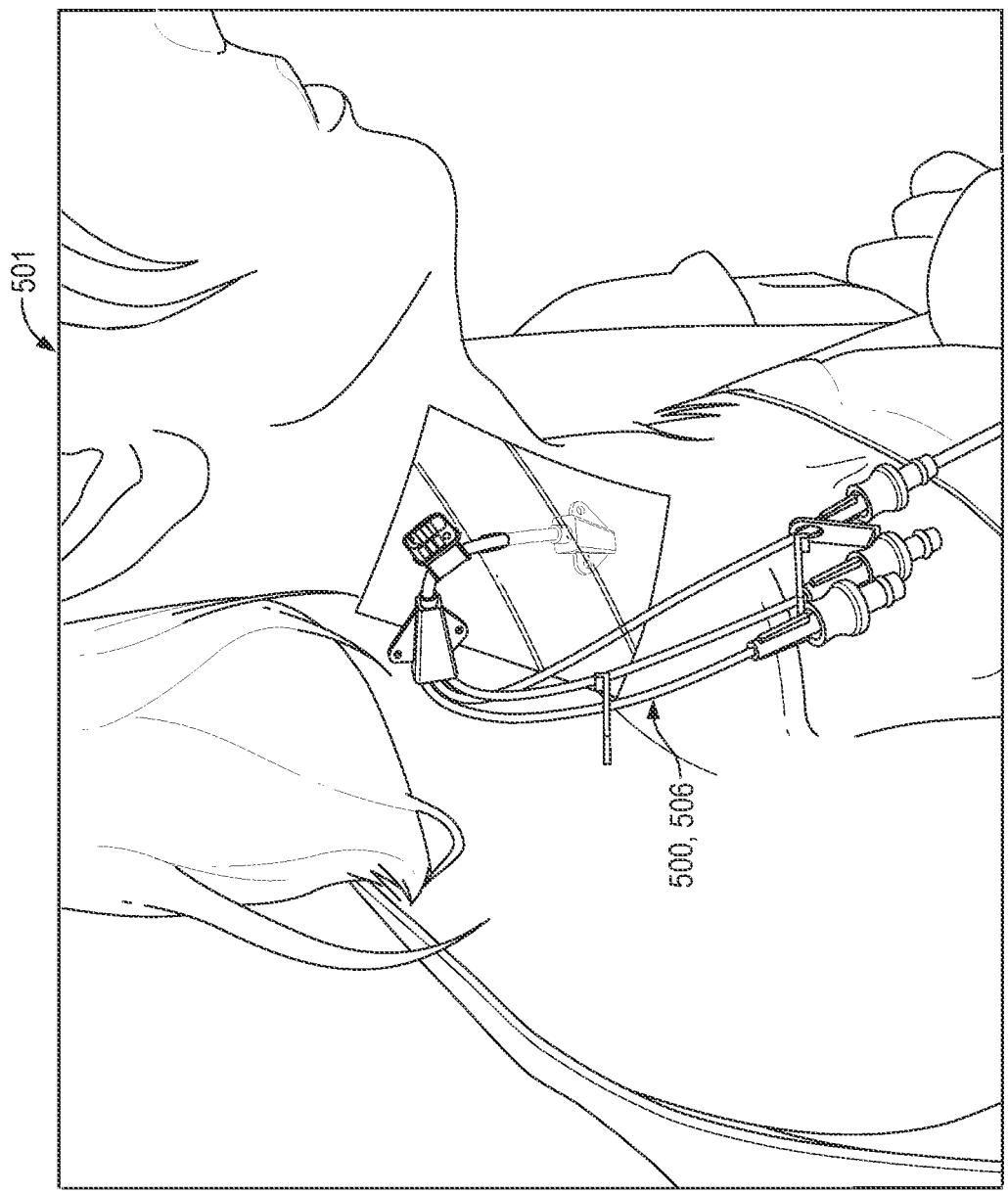
FIG. 5C is a perspective view illustrating use on a patient of a central venous catheter made in accordance with the present invention.

Referring to FIGS. 5C, illustrates use on a patient 501 of a central venous catheter 500, 506 made in accordance with the present invention, illustrating the wall 504 of the catheter 500, 506 transmitting light from the light emitter 24 to an exterior portion of the patient's 501 skin and into the patient's 501 body.

Figure 5D:
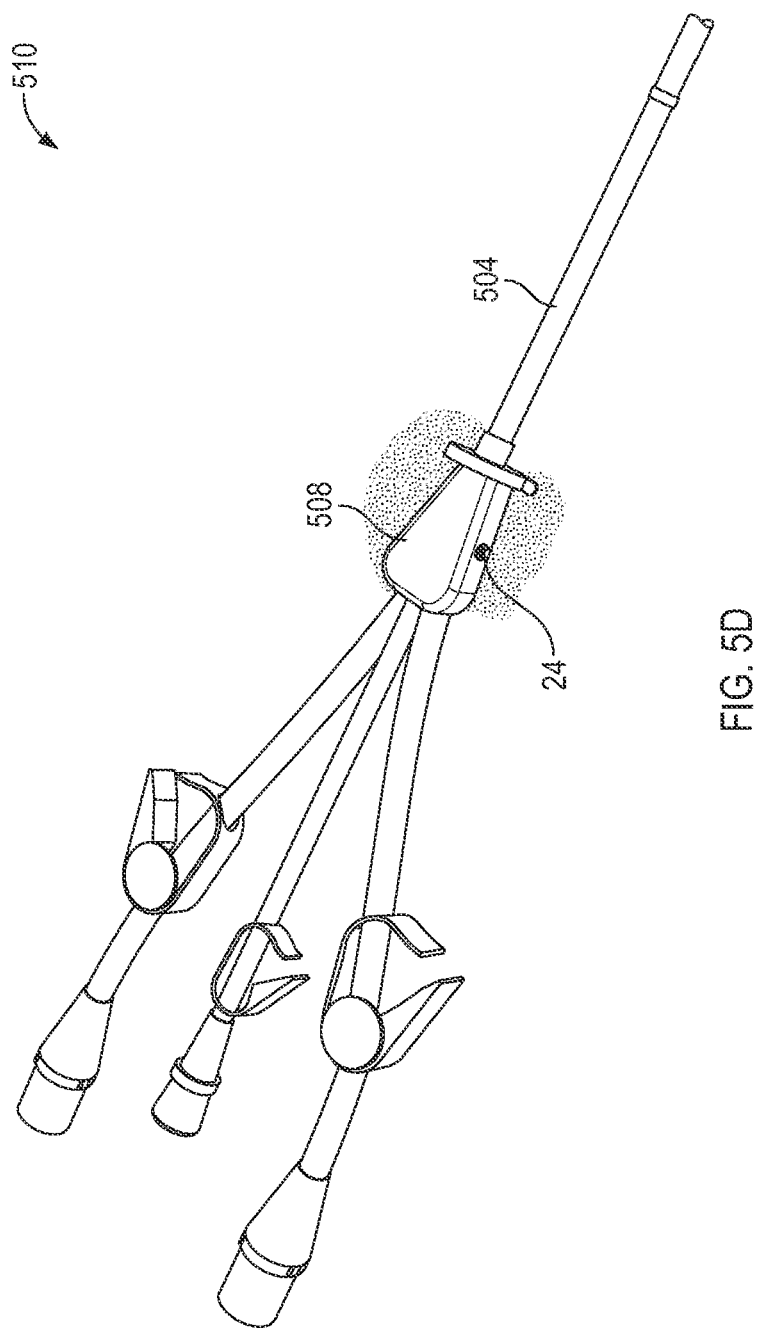
FIG. 5D is a partial perspective view of an exemplary embodiment of a central venous catheter made in accordance with the present invention with an integral light emitter.

Referring to FIG. 5D, an exemplary embodiment of a central venous catheter made in accordance with the present invention is illustrated generally at 510. The catheter 510 includes a wall 504 and a hub 508 comprising an optically transparent material. The hub 508 includes an integral light emitter 24 configured to emit light through the wall 504 and hub 508.

Figure 5E:
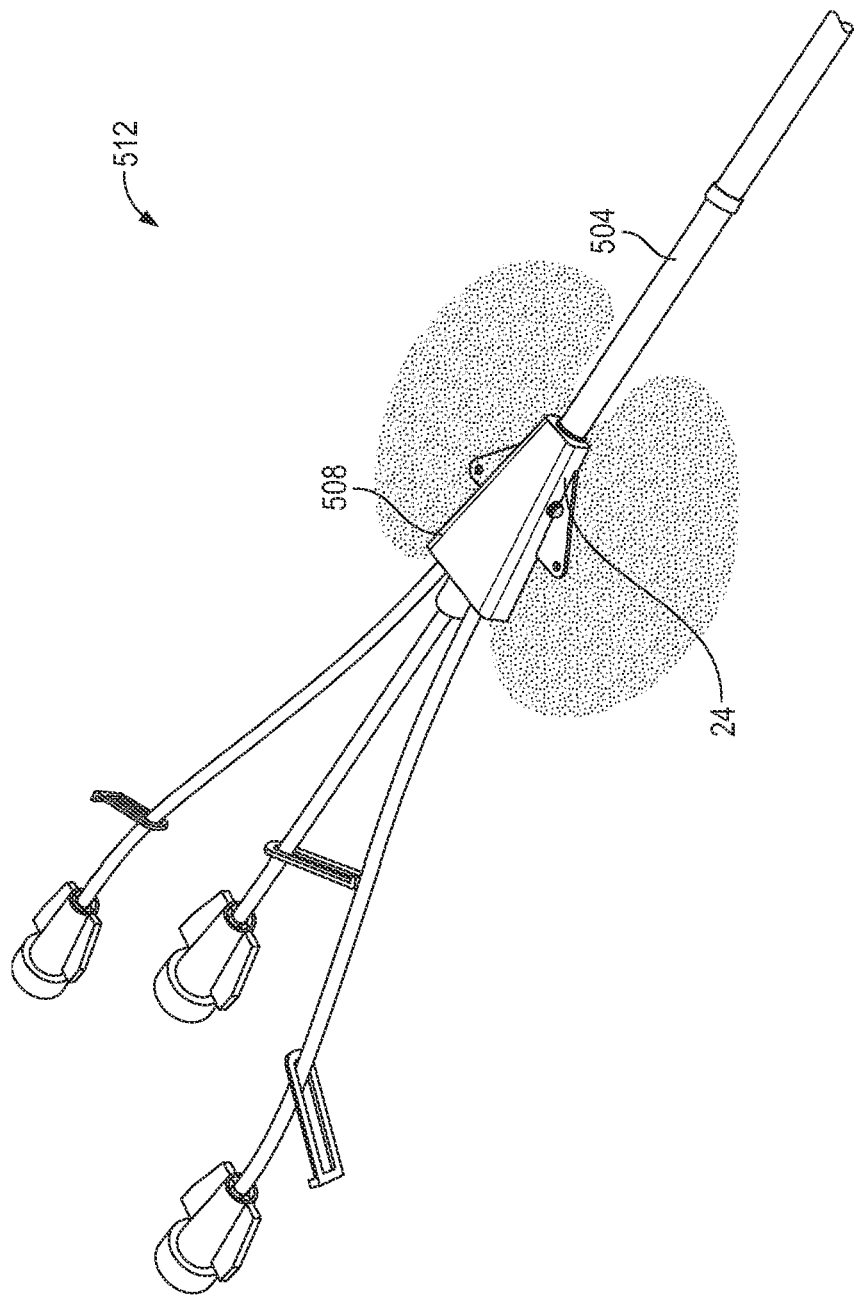
FIG. 5E is a partial perspective view of another exemplary embodiment of a central venous catheter made in accordance with the present invention with an integral light emitter.

Referring to FIG. 5E, another exemplary embodiment of a central venous catheter made in accordance with the present invention is illustrated generally at 512. The catheter 512 includes a wall 504 and a hub 508 comprising an optically transparent material. The hub 508 includes an integral light emitter 24 configured to emit light through the wall 504 and hub 508.

Figure 5F:
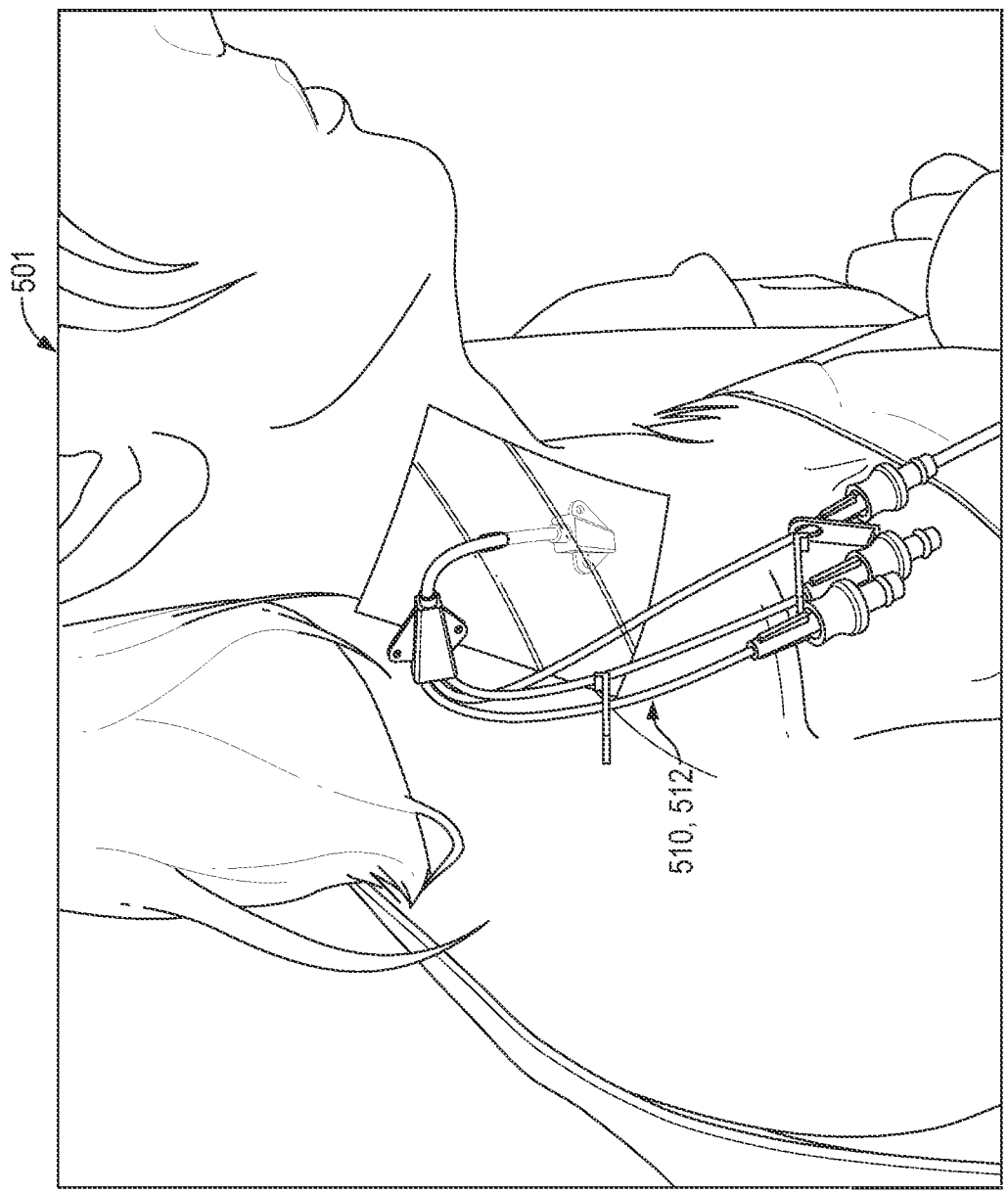
FIG. 5F is a perspective view illustrating use on a patient of a central venous catheter made in accordance with the present invention.

Referring to FIG. 5F, illustrates use on a patient 501 of a central venous catheter 510, 512 made in accordance with the present invention, showing the skin around the hub 508 of the catheter 510, 512, receiving exposure to additional light from the integral light emitter 24, in addition to light transmitted through the wall 504 to an exterior portion of the patient's 501 skin and into the patient's 501 body.

Figure 6B:
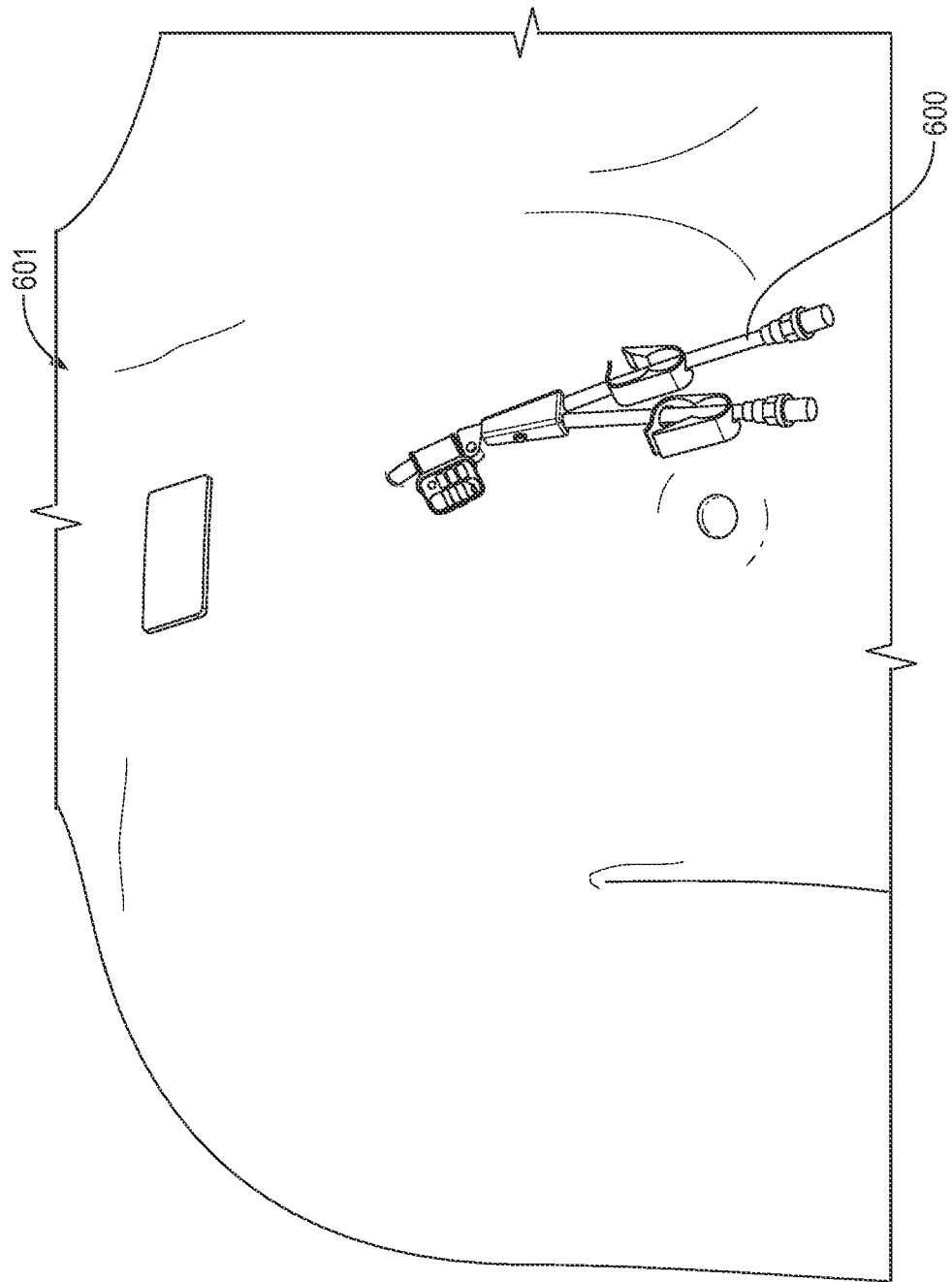
FIG. 6B is a perspective view illustrating use on a patient of a long-term hemodialysis catheter made in accordance with the present invention.

Referring to FIGS. 6A and 6B, an exemplary embodiment of a hemodialysis catheter made in accordance with the present invention is illustrated generally at 600 and in use on a patient 601. The catheter 600 includes a wall 604 comprising an optically transparent material and a light emitter 24 configured to emit light through the wall 604. The light emitter 24 may include a display 41 for viewing the function settings 37, 38, 39 of the control circuit 30 of the light emitter 24.

Figure 6C:
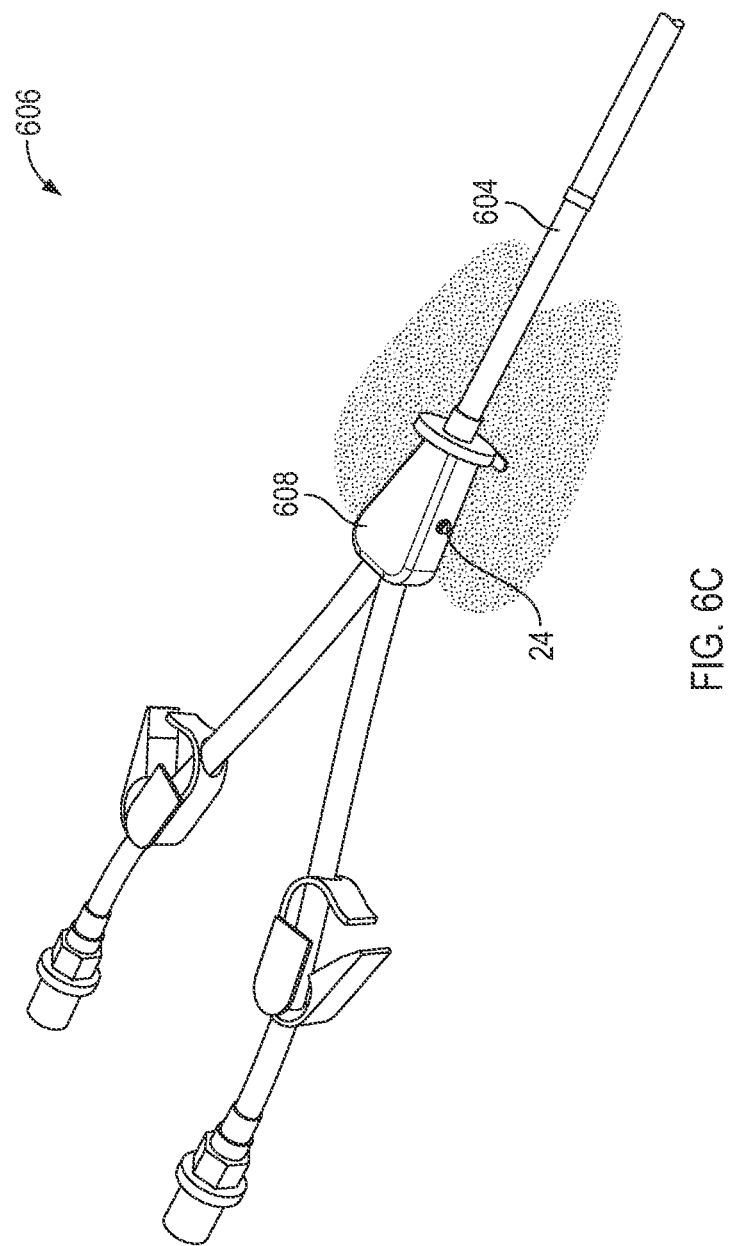
FIG. 6C is a partial perspective view of another exemplary embodiment of a long-term hemodialysis catheter made in accordance with the present invention having an integral light emitter.

Referring to FIGS. 6C and 6D, another exemplary embodiment of a hemodialysis catheter made in accordance with the present invention is illustrated generally at 606 and in use on a patient 601. The catheter 606 includes a wall 604 and a hub 608 comprising an optically transparent material and a light emitter 24 configured to emit light through the wall 604 and hub 608.

Figure 7A:
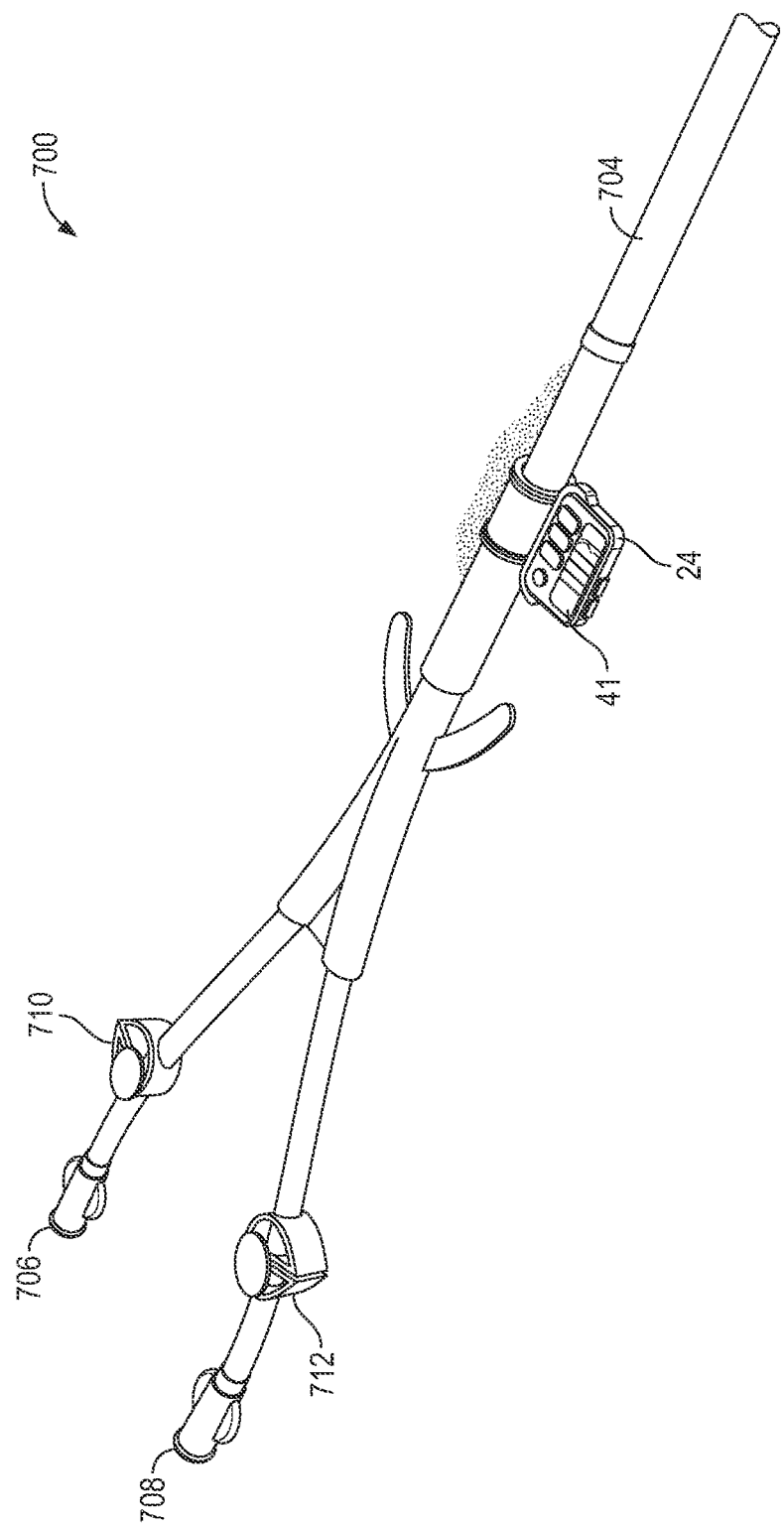
FIG. 7A is a partial perspective view of an exemplary embodiment of a PICC line made in accordance with the present invention.
Figure 7B:
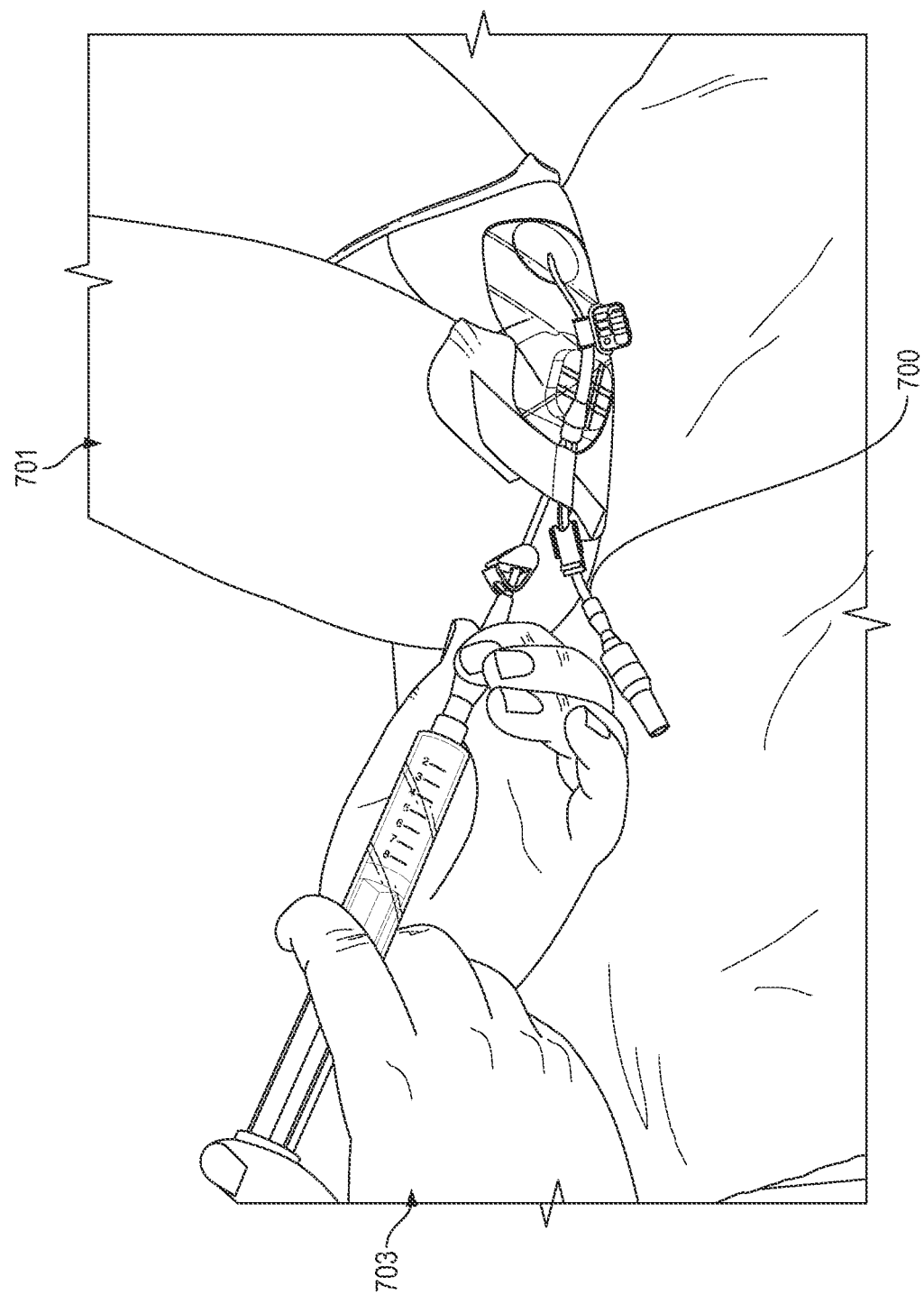
FIG. 7B is a perspective view illustrating use on a patient of a PICC line made in accordance with the present invention.

Referring to FIGS. 7A and 7B, an exemplary embodiment of a peripherally inserted central catheter (PICC) line made in accordance with the present invention is illustrated generally at 700 and in use on a patient 701. A medical professional 703 may administer medications through a port 706, 708 of the PICC line 700. The ports may be selectively closed with clamps 710, 712. The PICC line 700 includes a wall 704 comprising an optically transparent material and a light emitter 24 configured to emit light through the wall 704. The light emitter 24 may include a display 41 for viewing the function settings 37, 38, 39 of the control circuit 30 of the light emitter 24.

Figure 7C:
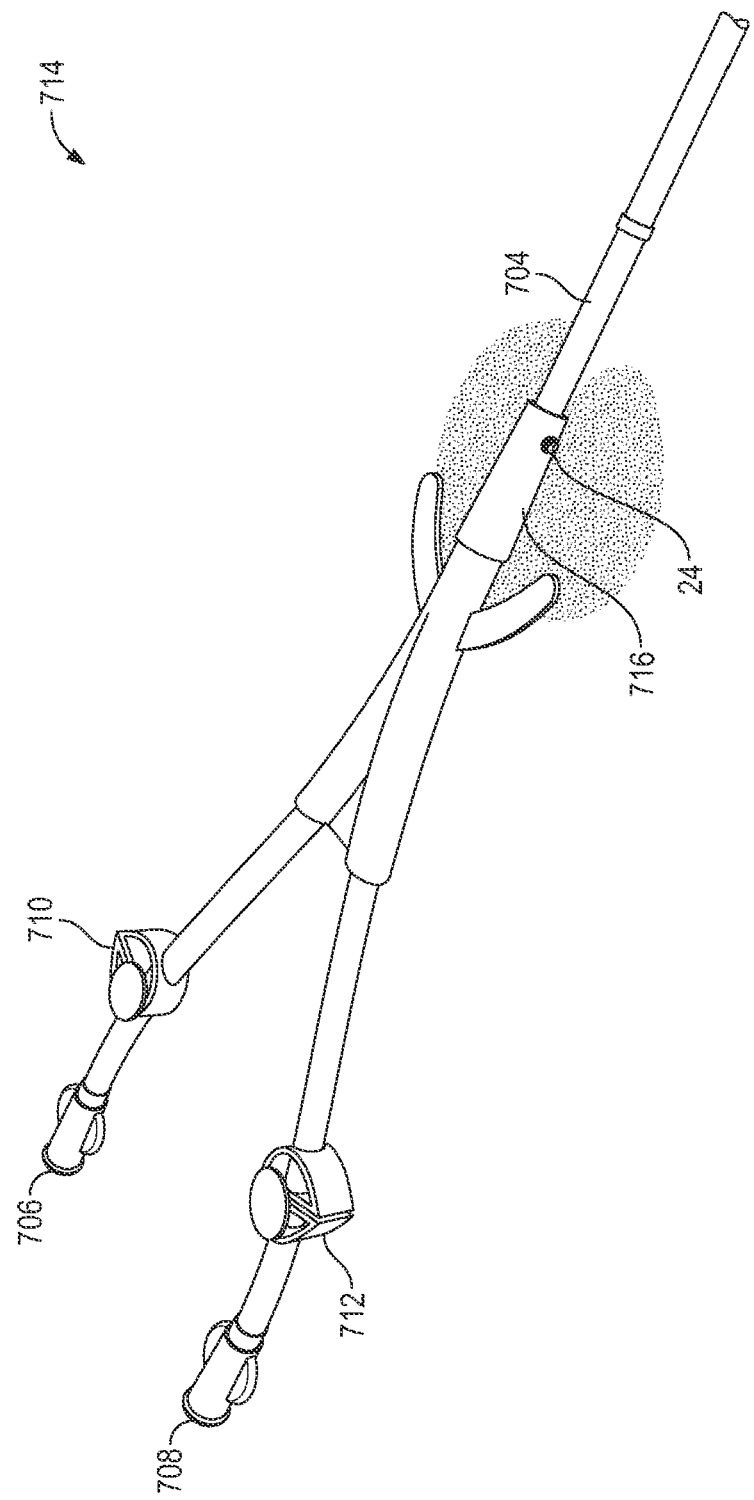
FIG. 7C is a partial perspective view of another exemplary embodiment of a PICC line made in accordance with the present invention, having an integral light emitter.
Figure 7D:
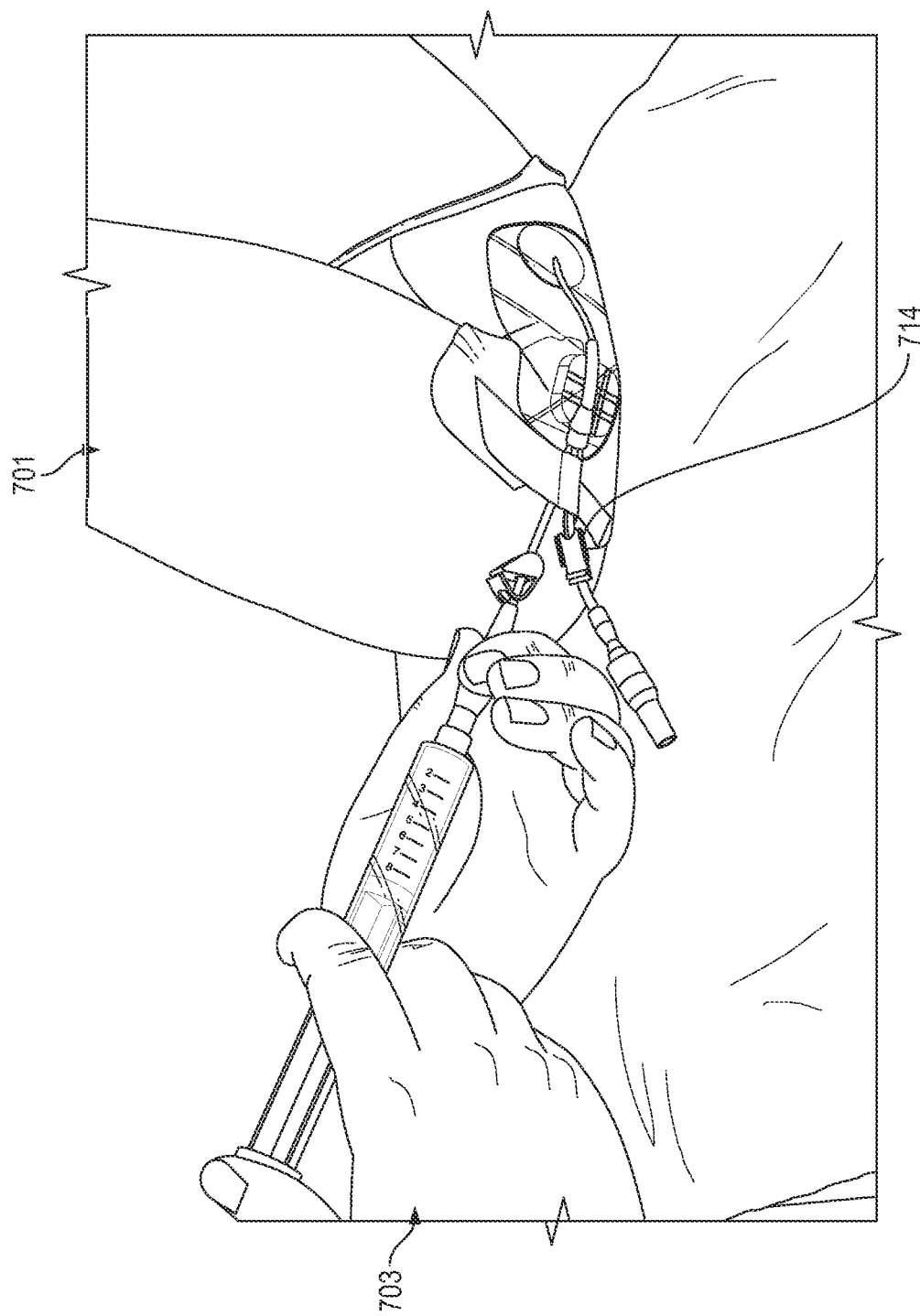
FIG. 7D is a partial perspective view illustrating use on a patient of another embodiment of a PICC line made in accordance with the present invention, having an integral light emitter.

Referring to FIGS. 7C and 7D, another exemplary embodiment of a PICC line made in accordance with the present invention is illustrated generally at 714 and in use on a patient 701. A medical professional 703 may administer medications through a port 706, 708 of the PICC line 700. The ports may be selectively closed with clamps 710, 712. The PICC line 700 includes a wall 704 and a hub 716 comprising an optically transparent material and a light emitter 24, integrated with the hub 716, configured to emit light through the wall 704 and hub 716. The light emitter 24 may include a display 41 for viewing the function settings 37, 38, 39 of the control circuit 30 of the light emitter 24.

Figure 7E:
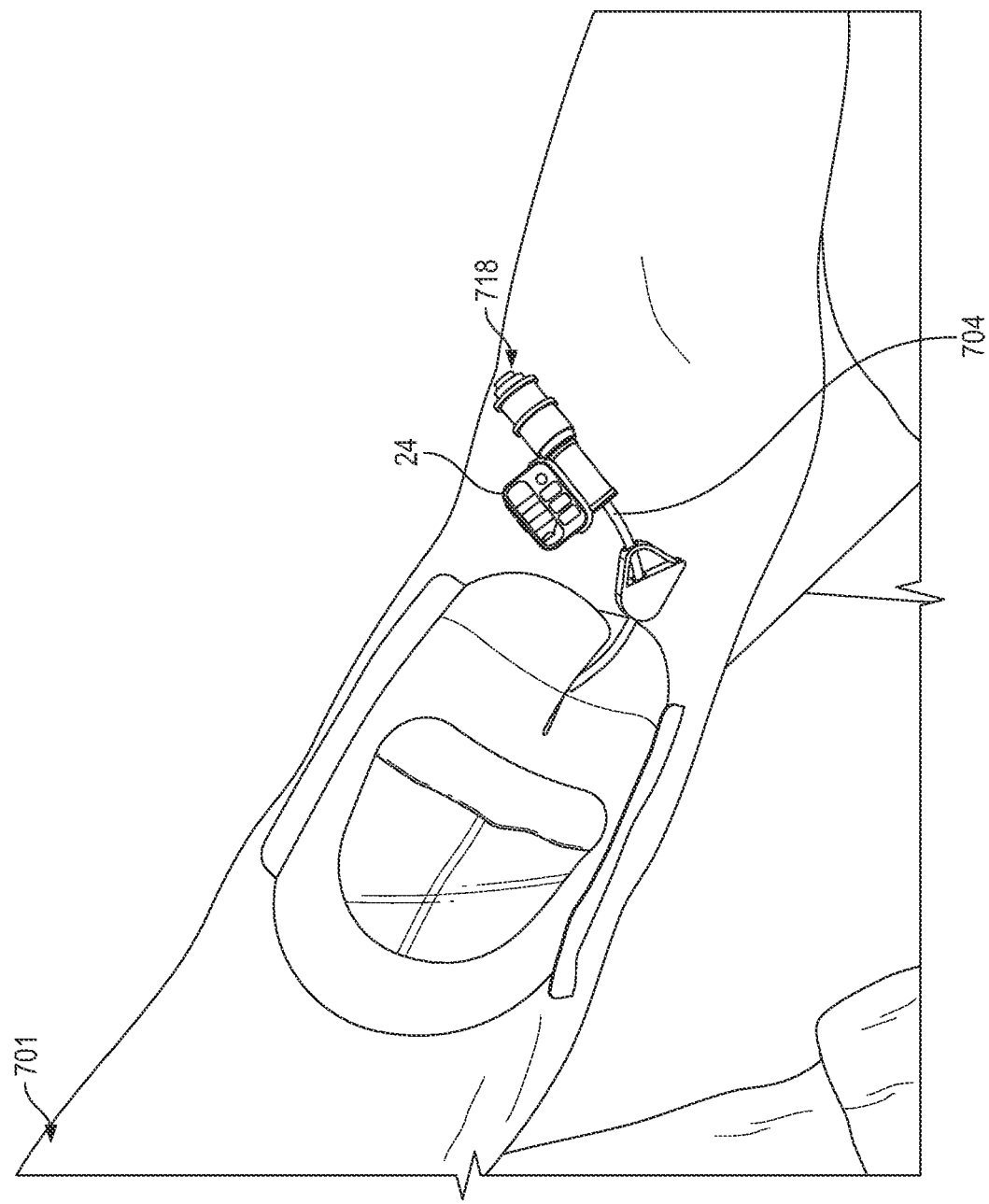
FIG. 7E, is a partial perspective view illustrating use on a patient of yet another embodiment of a PICC line made in accordance with the present invention.
Figure 8A:
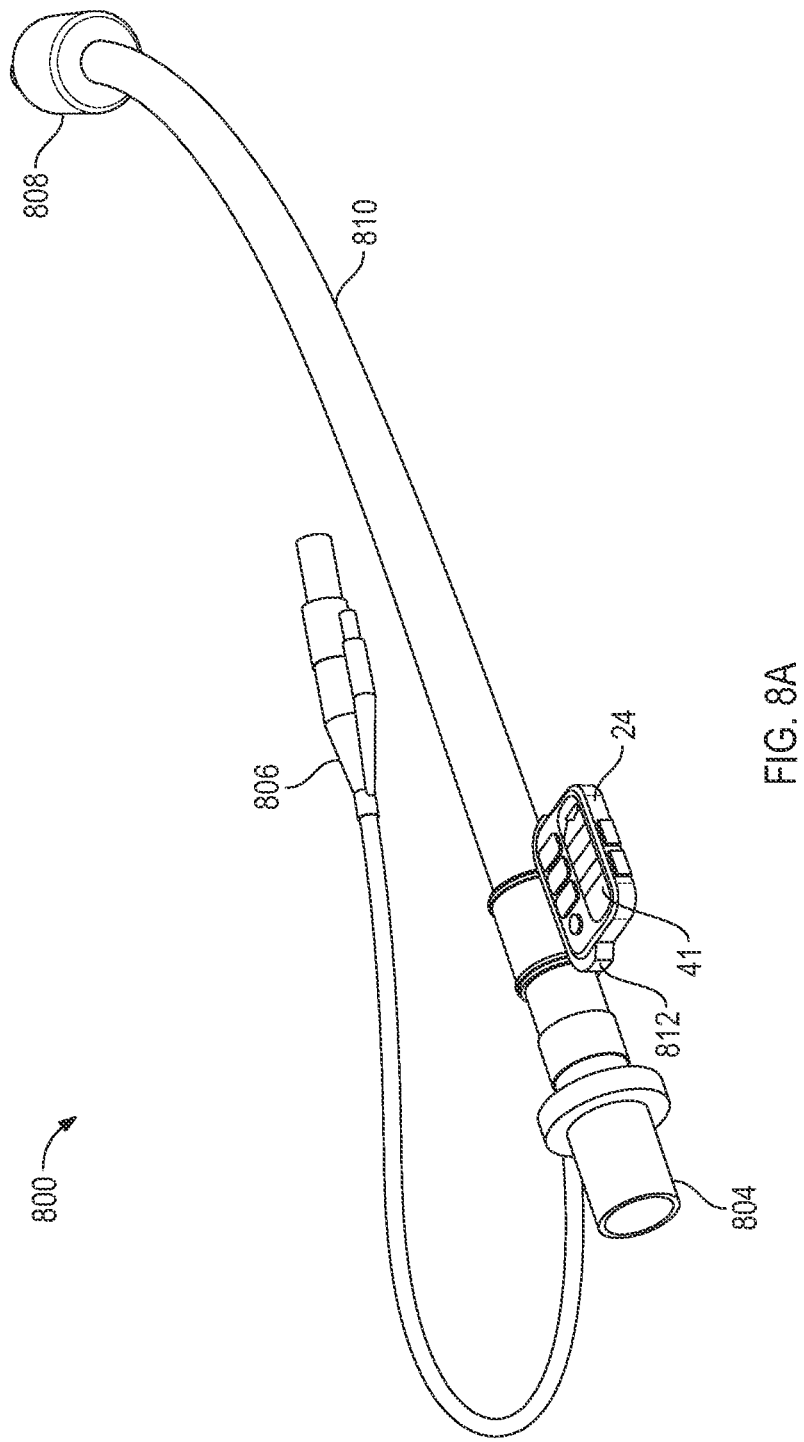
FIG. 8A is a perspective view of an exemplary embodiment of an endotracheal tube made in accordance with the present invention, with a removable light emitter attached thereto.
Figure 8B:
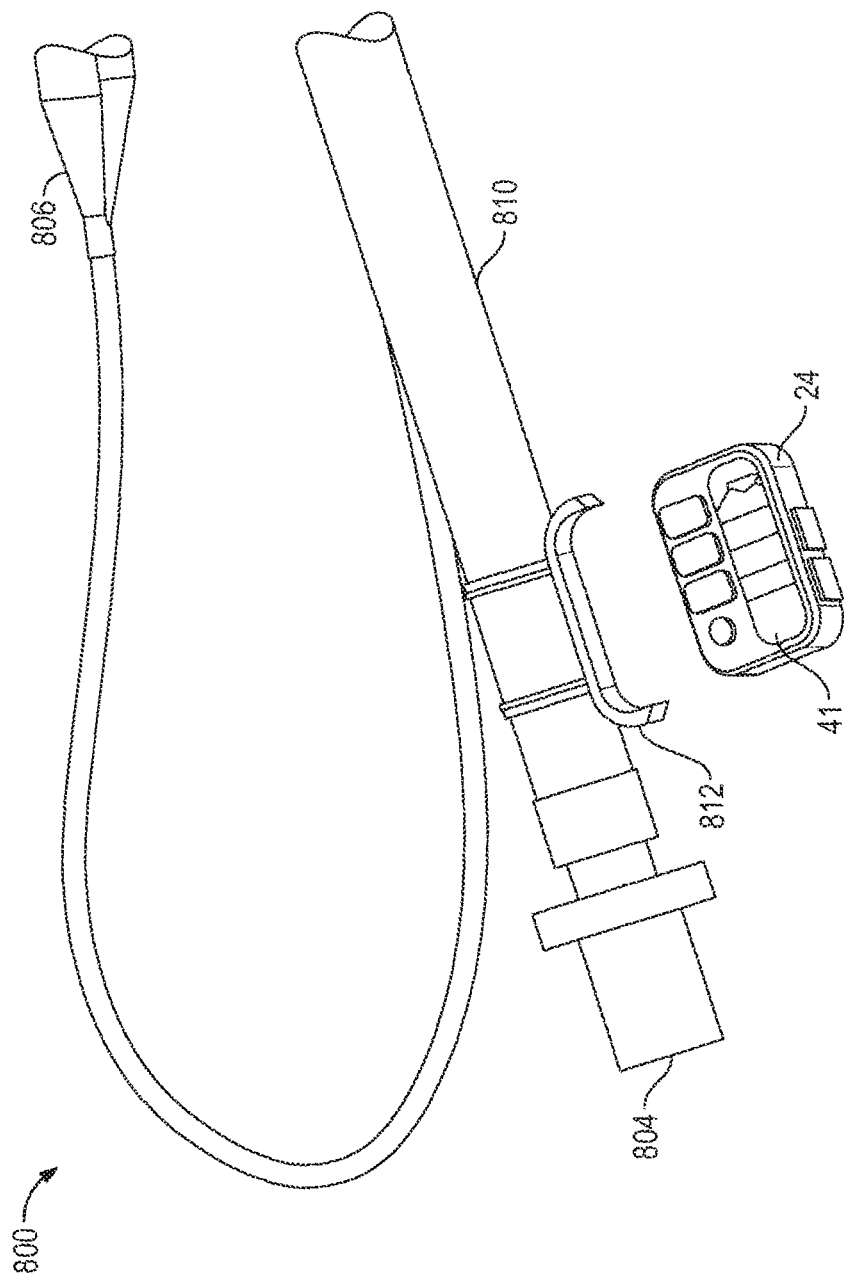
FIG. 8B is a perspective view of an exemplary embodiment of an endotracheal tube made in accordance with the present invention, illustrating a light emitter detached therefrom.
Figure 8D:
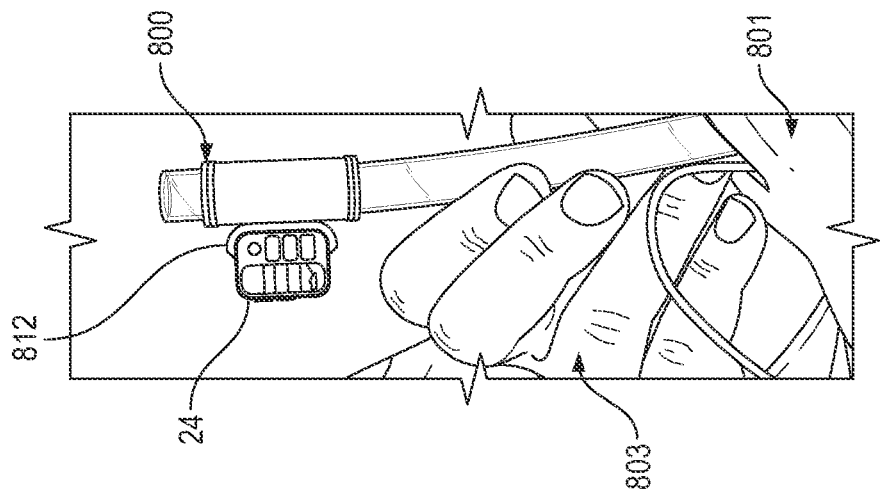
FIG. 8D is a partial perspective view illustrating an intubated patient with an endotracheal tube made in accordance with the present invention, with the light emitter attached.
Figure 8C:
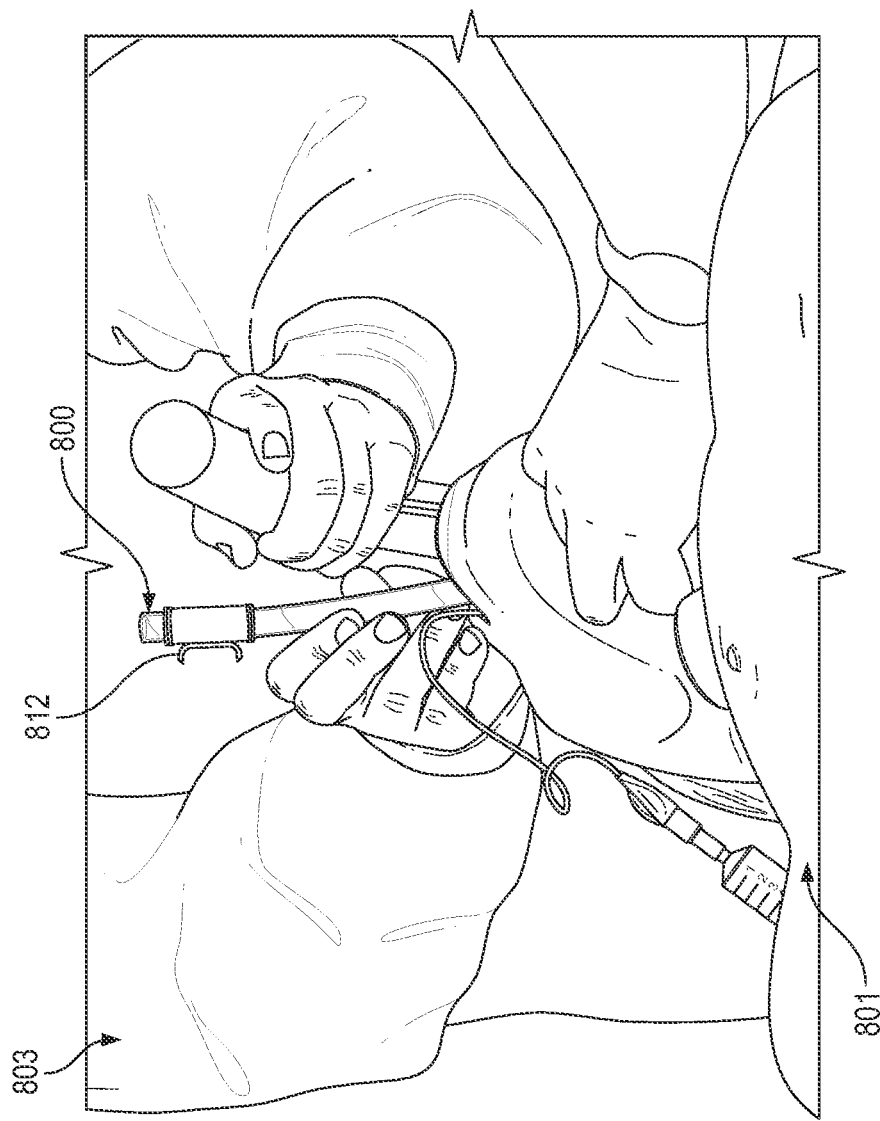
FIG. 8C is a partial perspective view illustrating intubation of a patient with an endotracheal tube made in accordance with the present invention, with the light emitter removed.

Referring to FIG. 7E, yet another alternative embodiment of a PICC line is illustrated at 718 being used on a patient 701.

Referring to FIGS. 8A-8D, an exemplary embodiment of a endotracheal tube made in accordance with the present invention is illustrated generally at 800 and in use on a patient 801 by a medical professional 803. The endotracheal tube 800 includes a port 804 for delivery of fluids and nutrition to the patient and inflation tube port 806 for inflating an inflation cuff 808 at a distal end of the tube 800. The tube 800 includes a wall 810 comprising an optically transparent material and a light emitter 24 configured to emit light through the wall 804. The light emitter 24 may include a display 41 for viewing the function settings 37, 38, 39 of the control circuit 30 of the light emitter 24. During intubation, the light emitter 24 may be removed from the tube 800 to provide a better view for the medical professional 803 (best seen in FIG. 8C). Once intubated, the light emitter 24 may be re-attached to the tube 800 (best seen in FIG. 8D). The light emitter 24 may couple to the tube 800 via a clip 812 attached to the tube 800. The clip 812 may comprise a resilient material, allowing mating formations of the clip 812 to clasp the housing 25 of the light emitter 24.

Figure 9A:
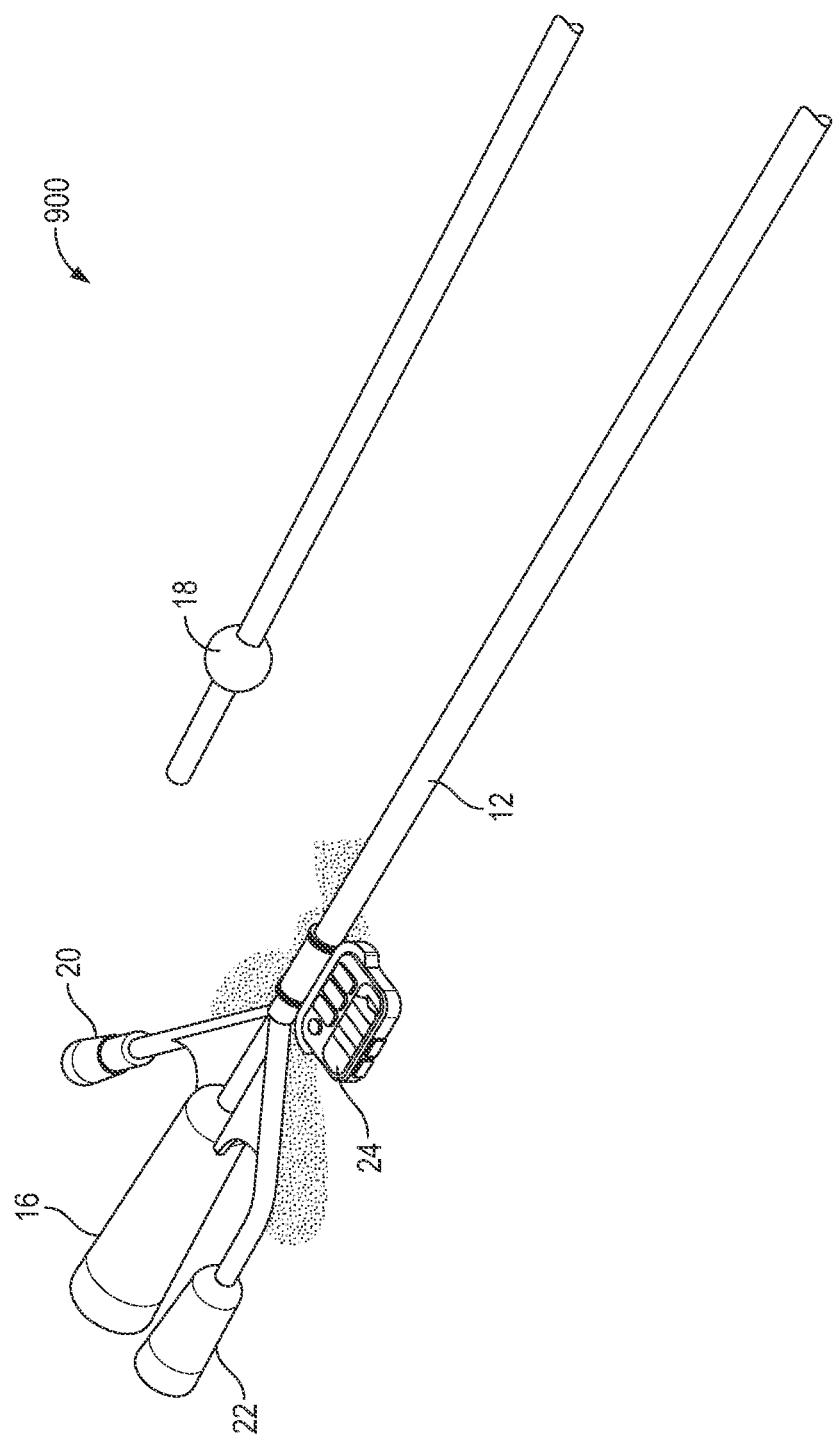
FIG. 9A is a partial perspective view of an exemplary embodiment of a urinary catheter made in accordance with the present invention.
Figure 9B:
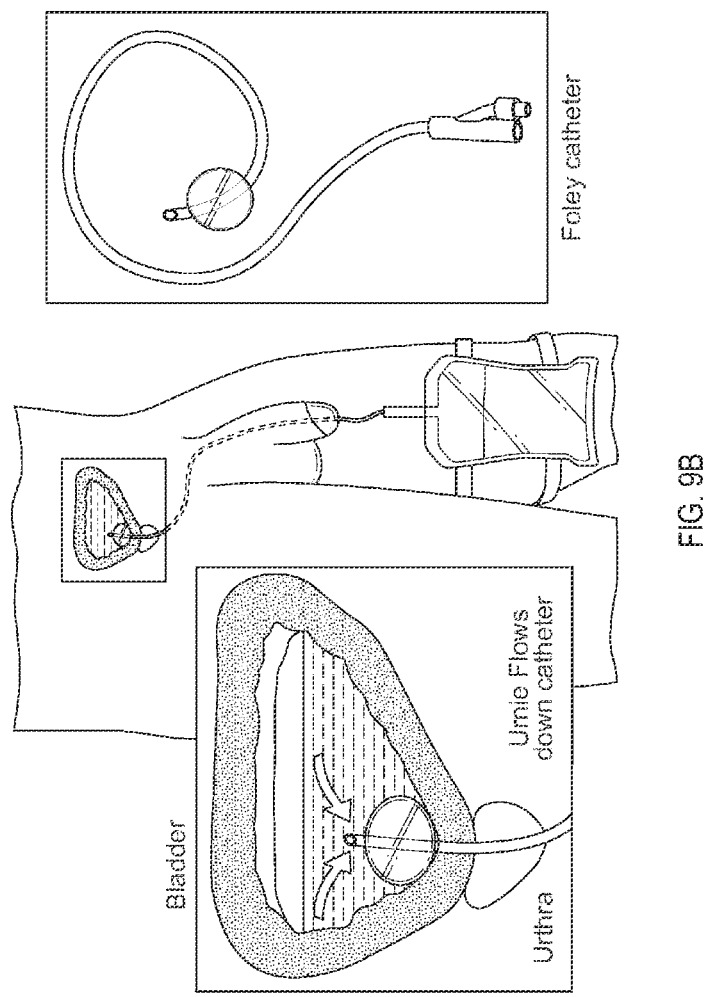
FIG. 9B is an illustration of use of a urinary catheter, generally.
Figure 9C:
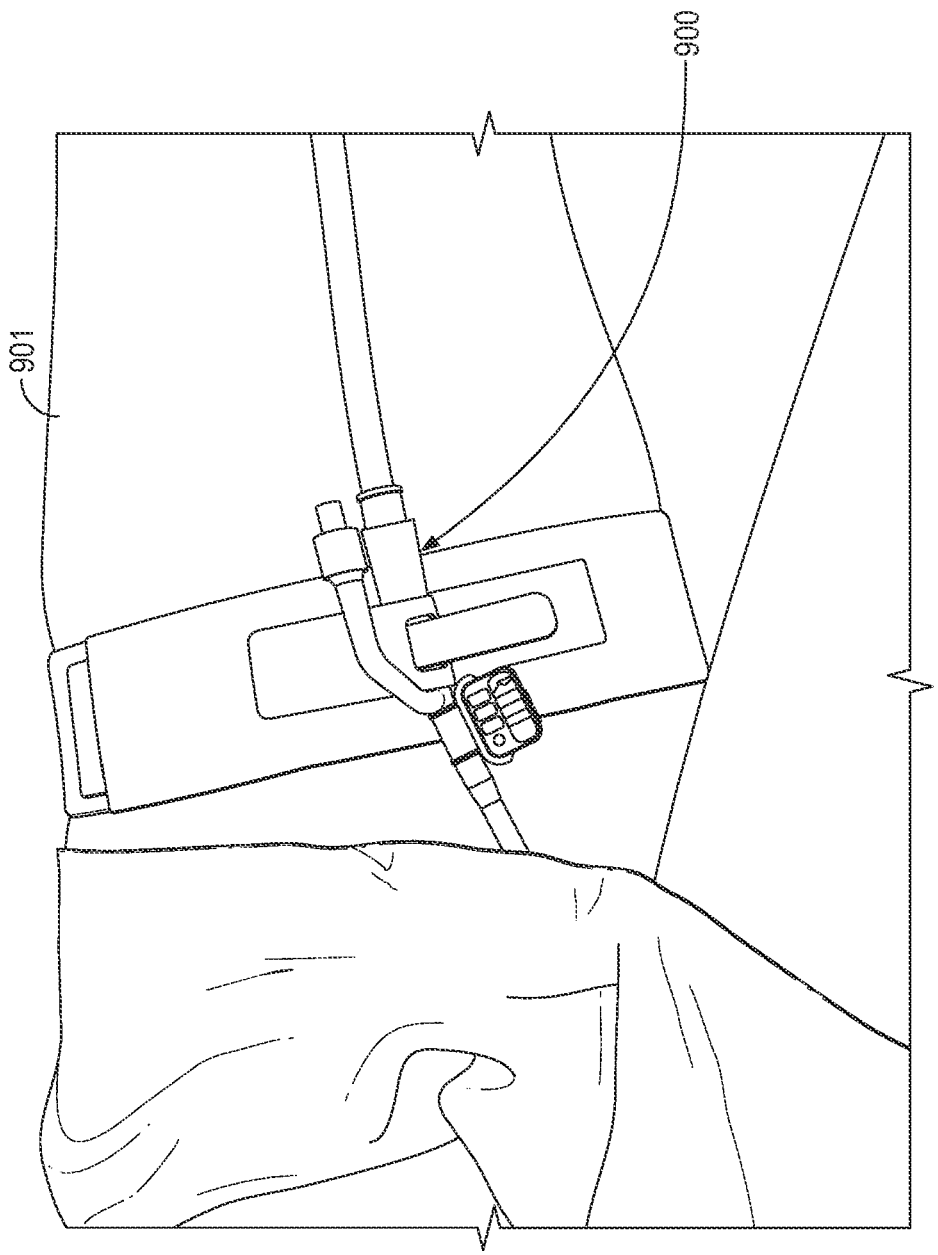
FIG. 9C is a perspective view illustrating use on a patient of a urinary catheter made in accordance with the present invention.
Figure 10A:
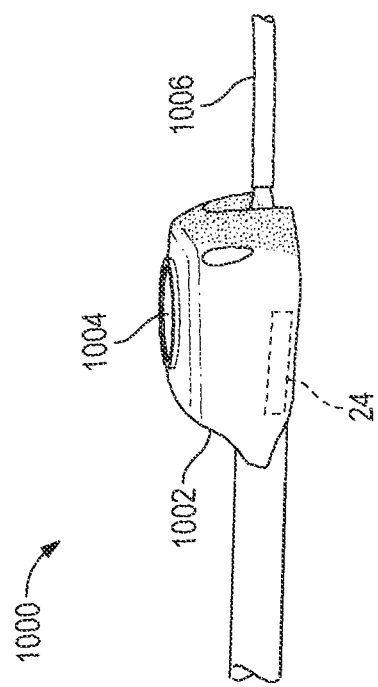
FIG. 10A is a front, side perspective view of an exemplary embodiment of a subdermal port made in accordance with the present invention.
Figure 10B:
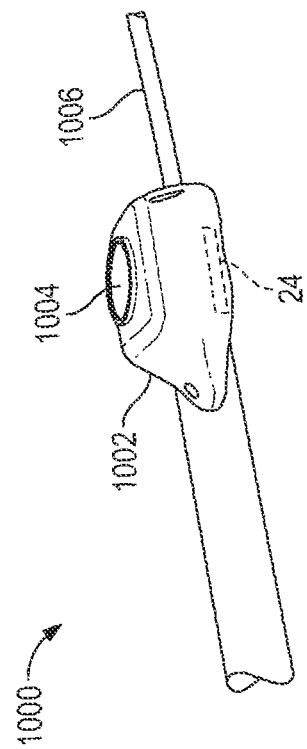
FIG. 10B is a rear, side perspective view of an exemplary embodiment of a subdermal port made in accordance with the present invention.
Figure 10D:
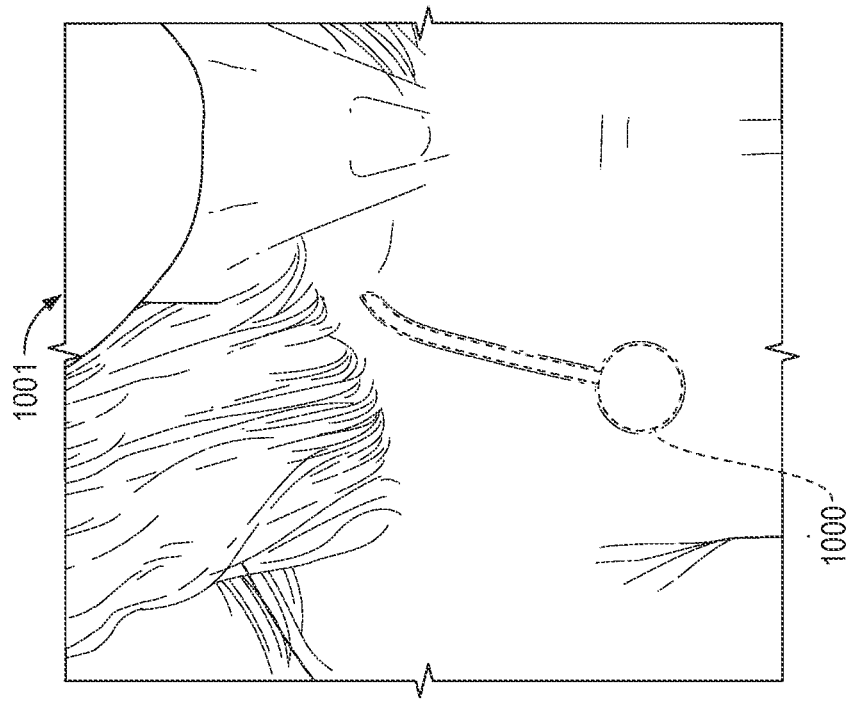
FIG. 10D is a perspective view illustrating use on a patient of a subdermal port made in accordance with the present invention, with the light emitter deactivated.
Figure 10C:
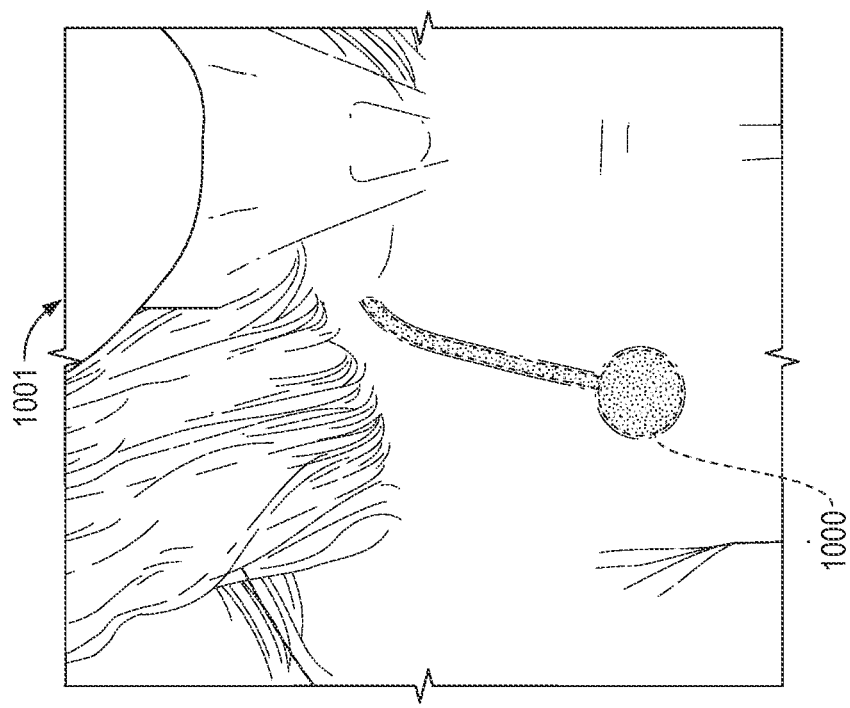
FIG. 10C is a perspective view illustrating use on a patient of a subdermal port made in accordance with the present invention, with the light emitter activated.

Referring to FIGS. 9A-9C, an exemplary embodiment of a urinary catheter made in accordance with the present invention is illustrated at 900 and in use on a patient 901. The catheter 900 includes an optically transparent tube 12 with a tip 14 and a drain 16. The catheter 10 may include an inflatable balloon 18 near the tip 14. An inflation port 20 is provided to inflate the balloon 18. In some configurations, the catheter 10 may include an irrigation port 22 as well. A light transmitter 24 is connected to the tube 12 and configured to emit light through the optically transparent wall of the catheter 10. The light emitter 24 may include a display 41 for viewing the function settings 37, 38, 39 of the control circuit 30 of the light emitter 24.

Referring to FIGS. 10A-10D, an exemplary embodiment of a subdermal port made in accordance with the present invention is illustrated at 1000 and in use on a patient 1001. The port 1000 includes a body 1002 with a septum 1004 and a catheter 1006. A light transmitter 24 may be incorporated into the body 1002 of the port 1000. The port 1000 may comprise an optically transparent material configured to transmit light emitted from the light transmitter 24. The light transmitter 24 may include a control circuit 30 where the on/off 36, timer function 37, intensity function 38 and/or wavelength function 39 are controlled wirelessly, magnetically, and/or sonically.

Figure 11A:
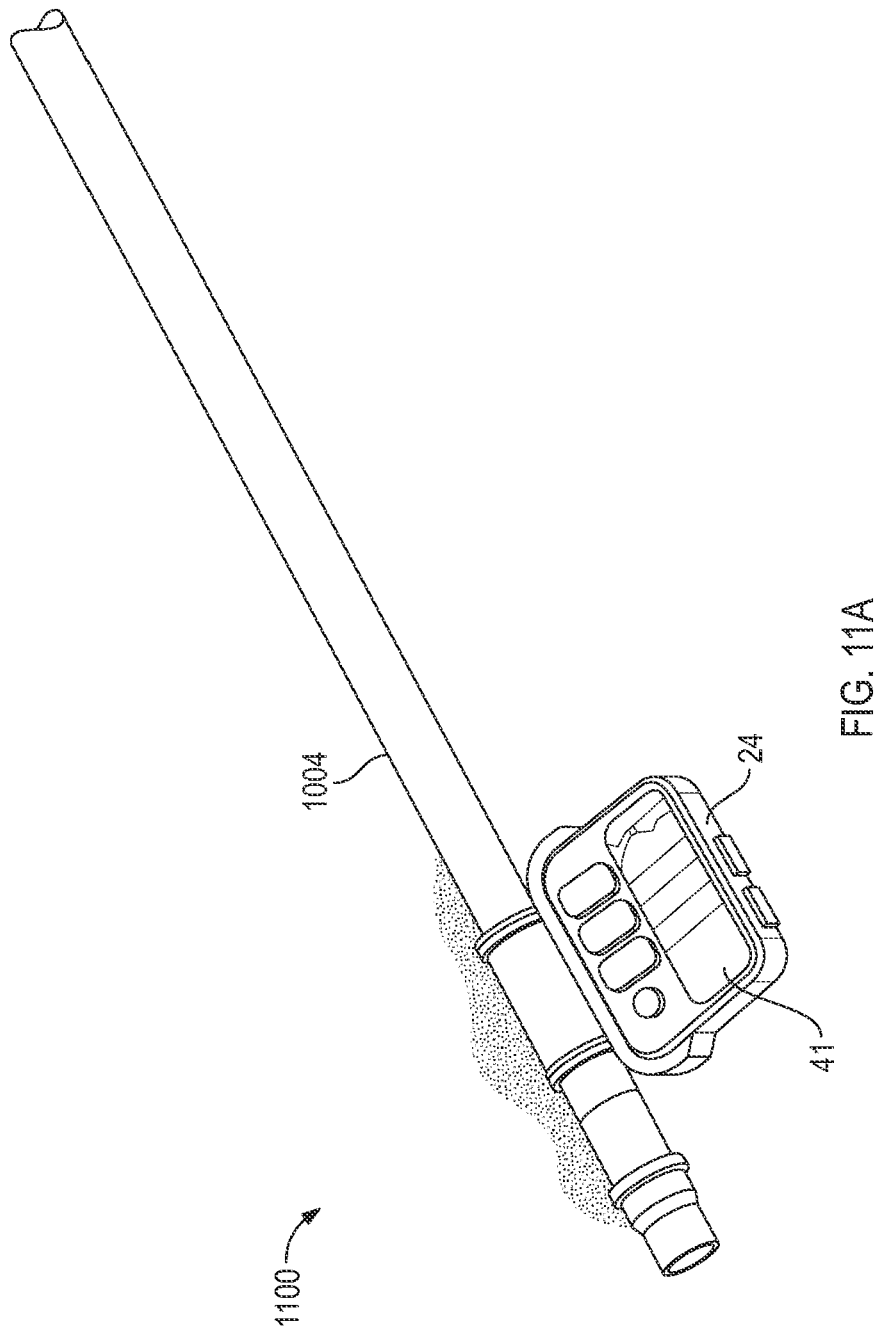
FIG. 11A is a partial perspective view of an exemplary embodiment of a Peritoneal dialysis catheter made in accordance with the present invention.
Figure 11B:
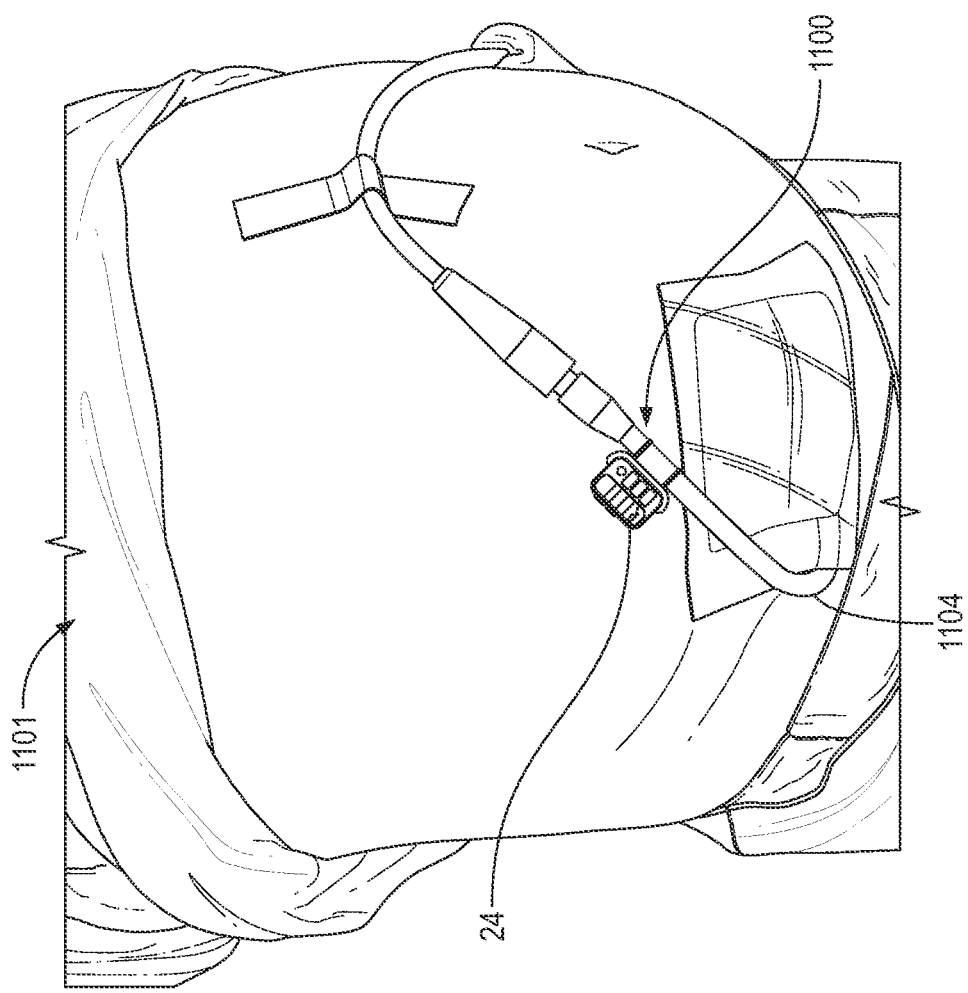
FIG. 11B is a partial perspective view illustrating use on a patient of a Peritoneal dialysis catheter made in accordance with the present invention.

Referring to FIGS. 11A-11B, an exemplary embodiment of a Peritoneal dialysis catheter made in accordance with the present invention is illustrated generally at 1100 and in use on a patient 1101. The catheter 1100 includes a wall 1104 comprising an optically transparent material and a light emitter 24 configured to emit light through the wall 1104. The light emitter 24 may include a display 41 for viewing the function settings 37, 38, 39 of the control circuit 30 of the light emitter 24.

Figure 12B:
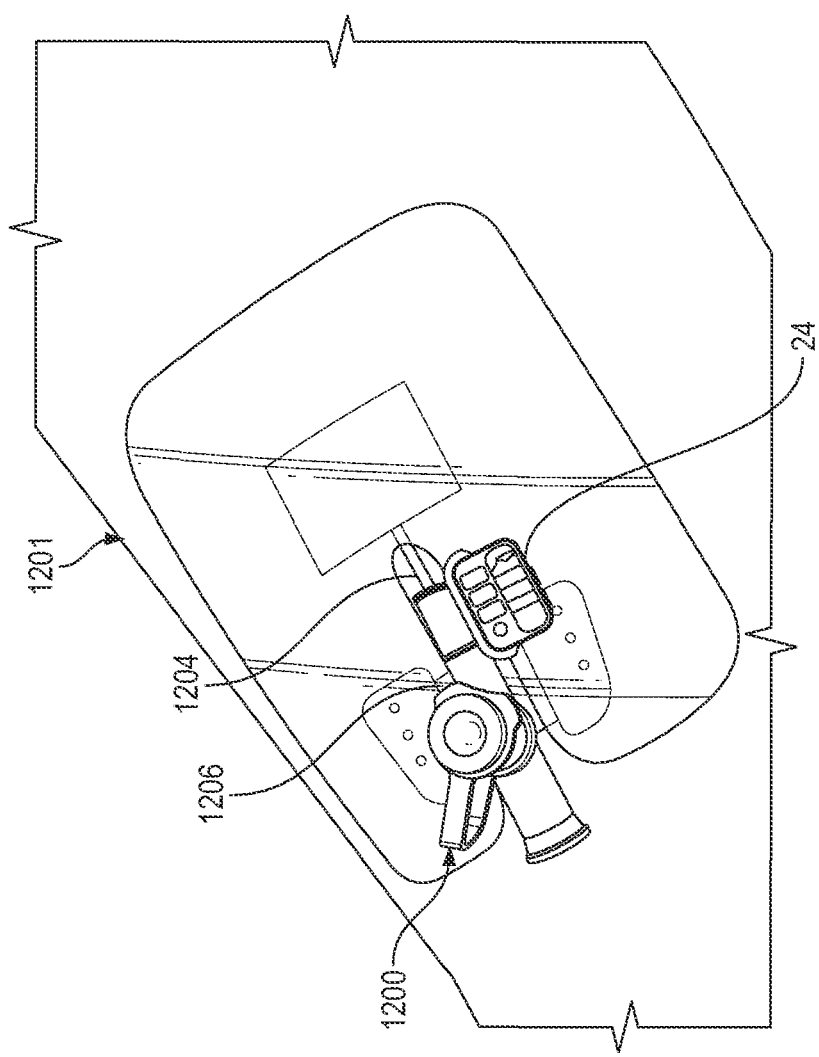
FIG. 12B is a perspective view illustrating use on a patient of a peripheral intravenous catheter made in accordance with the present invention.

Referring to FIGS. 12A-12B, an exemplary embodiment of a peripheral intravenous catheter made in accordance with the present invention is illustrated generally at 1200 and in use on a patient 1201. The catheter 1200 includes a wall 1204 and exterior portion 1206 comprising an optically transparent material and a light emitter 24 configured to emit light through the wall 1204 and exterior portion 1206. The light emitter 24 may include a display 41 for viewing the function settings 37, 38, 39 of the control circuit 30 of the light emitter 24.

Figure 13A:
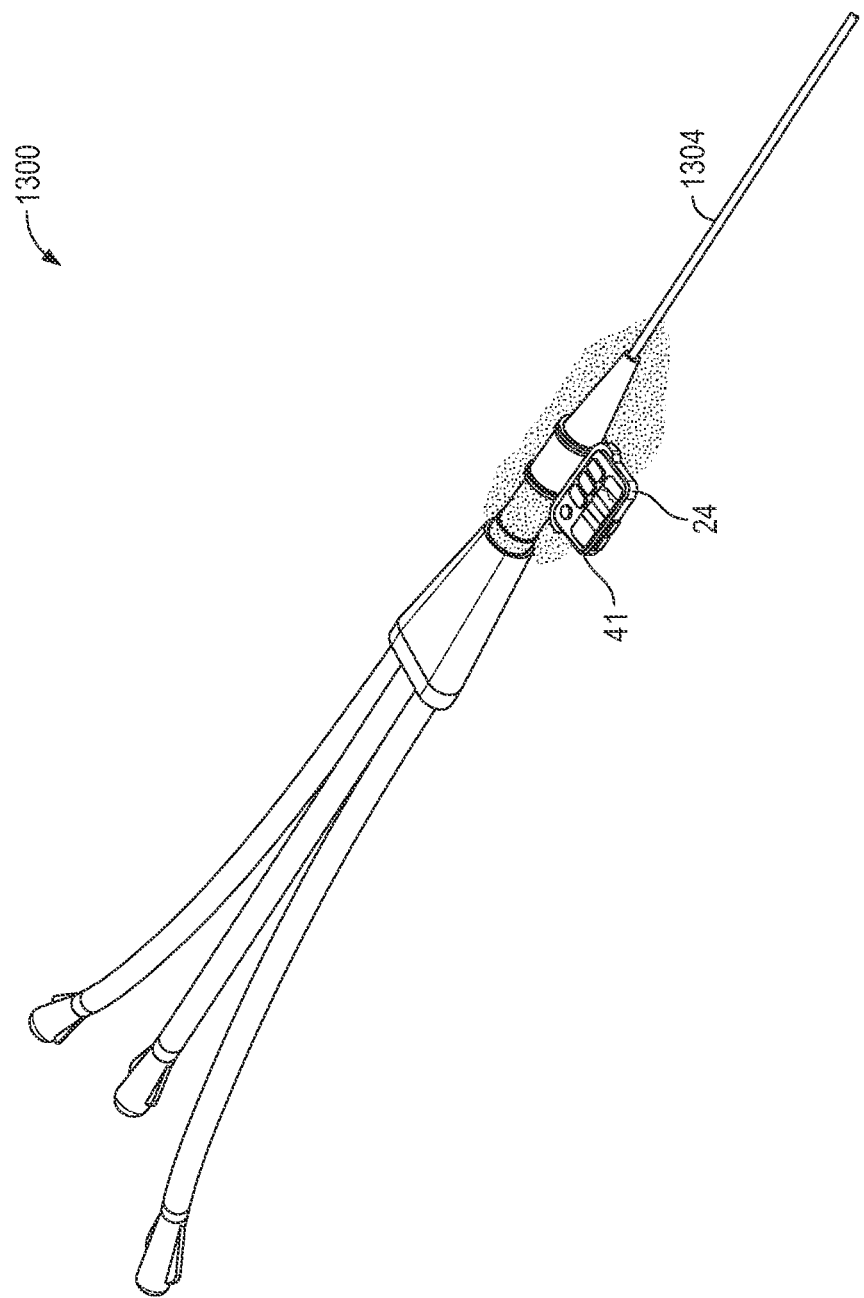
FIG. 13A is a partial perspective view of an exemplary embodiment of a short-term hemodialysis catheter made in accordance with the present invention.
Figure 13B:
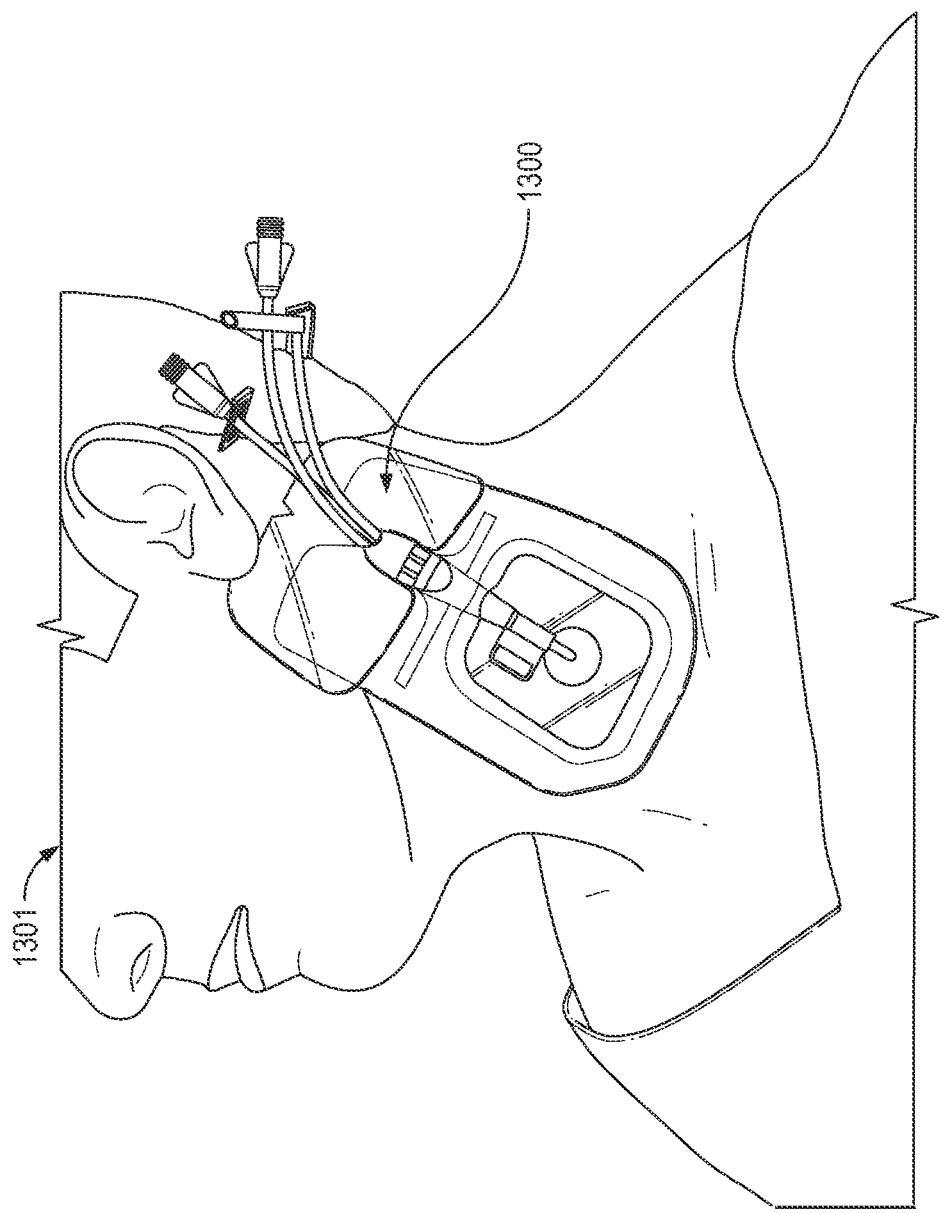
FIG. 13B is a perspective view illustrating use on a patient of a short-term hemodialysis catheter made in accordance with the present invention.

Referring to FIGS. 13A and 13B, an exemplary embodiment of a hemodialysis catheter made in accordance with the present invention is illustrated generally at 1300 and in use on a patient 1301. The catheter 1300 includes a wall 1304 comprising an optically transparent material and a light emitter 24 configured to emit light through the wall 1304. The light emitter 24 may include a display 41 for viewing the function settings 37, 38, 39 of the control circuit 30 of the light emitter 24.

Figure 13C:
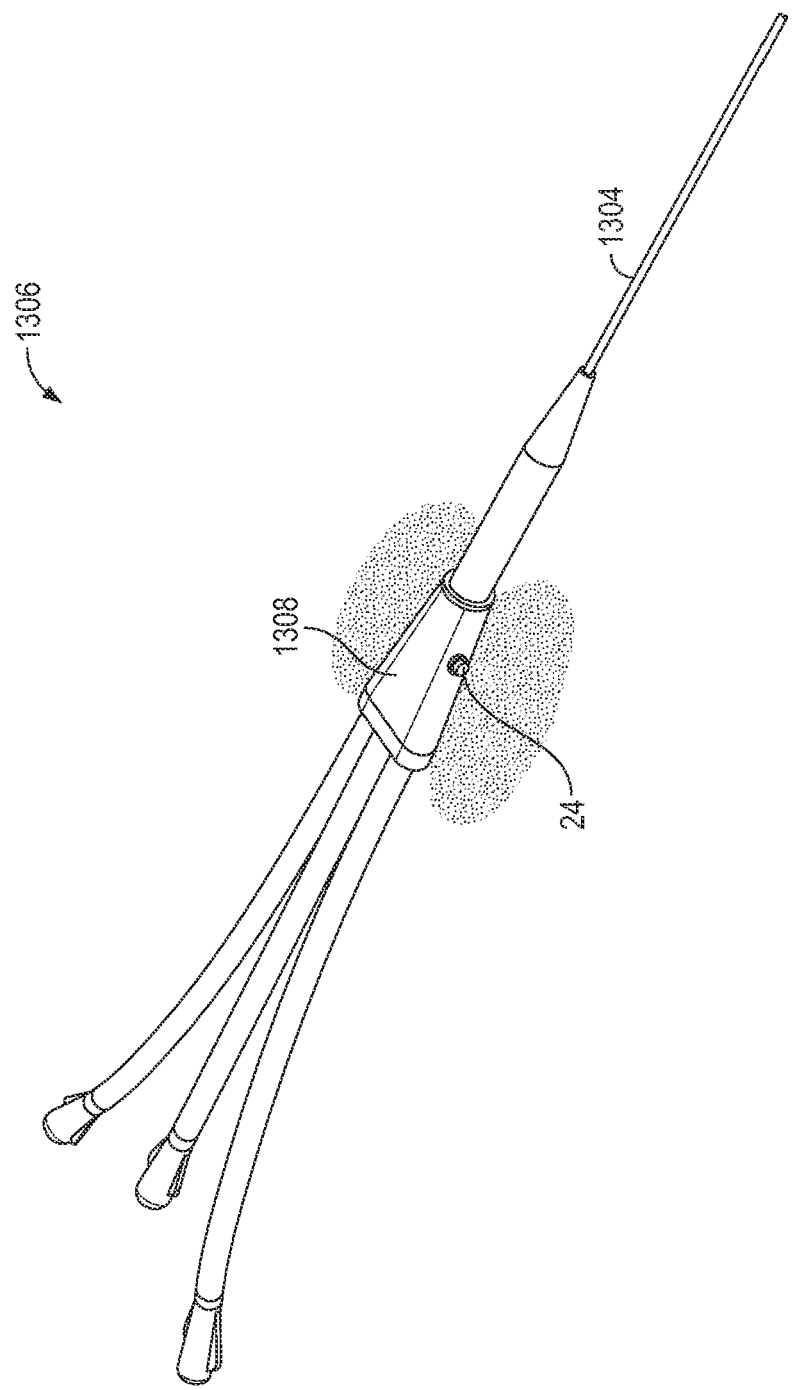
FIG. 13C is a partial perspective view of another exemplary embodiment of a short-term hemodialysis catheter made in accordance with the present invention having an integral light emitter.
Figure 13D:
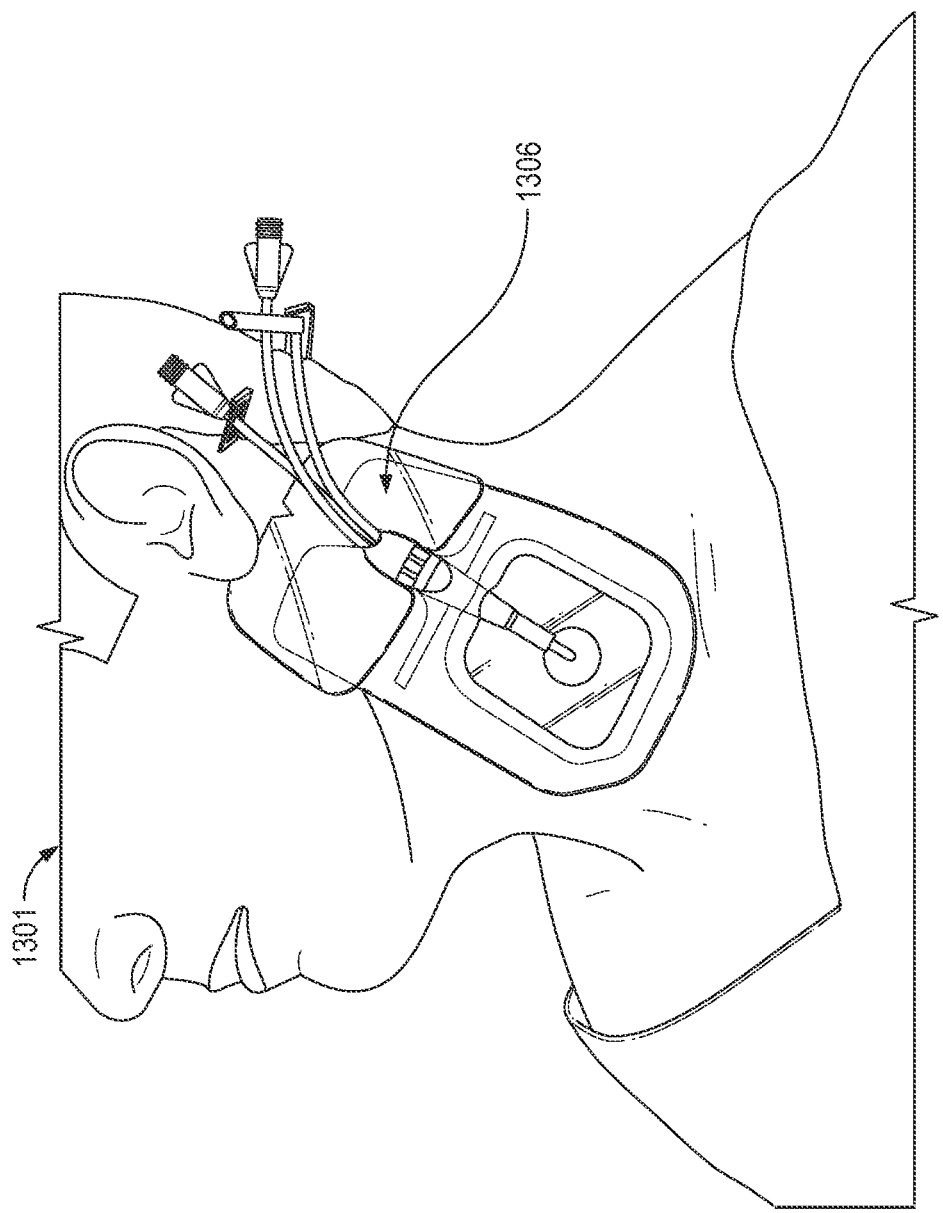
FIG. 13D is a perspective view illustrating use on a patient of a short-term hemodialysis catheter having an integral light emitter made in accordance with the present invention.

Referring to FIGS. 13C and 13D, another exemplary embodiment of a short-term hemodialysis catheter made in accordance with the present invention is illustrated generally at 1306 and in use on a patient 1301. The catheter 1306 includes a wall 1304 and a hub 1308 comprising an optically transparent material and a light emitter 24 configured to emit light through the wall 1304 and hub 1308.

Figure 14B:
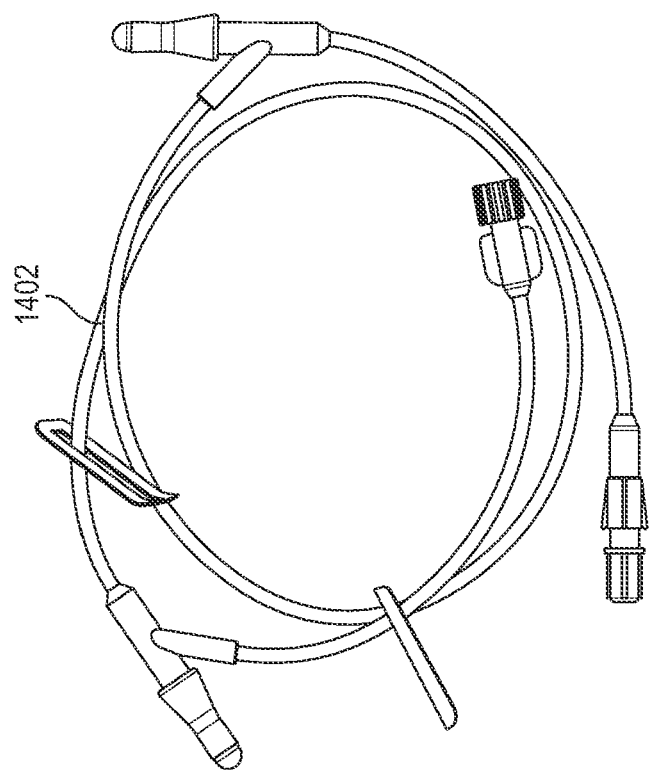
FIG. 14B is a perspective view of medical tubing that could a light emitter could be coupled thereto to create an antimicrobial effect.
Figure 14A:
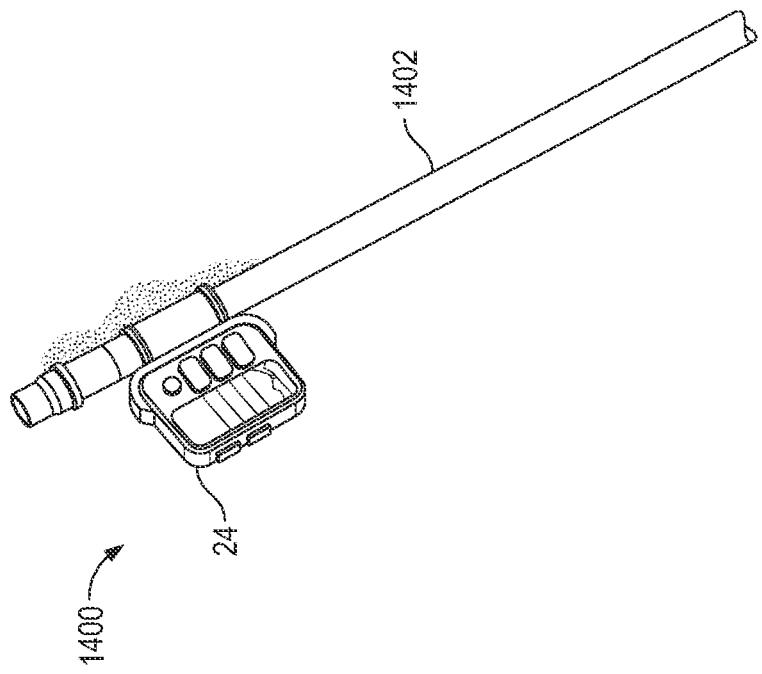
FIG. 14A is a perspective view illustrating use of a light emitter on medical tubing.
Figure 14C:
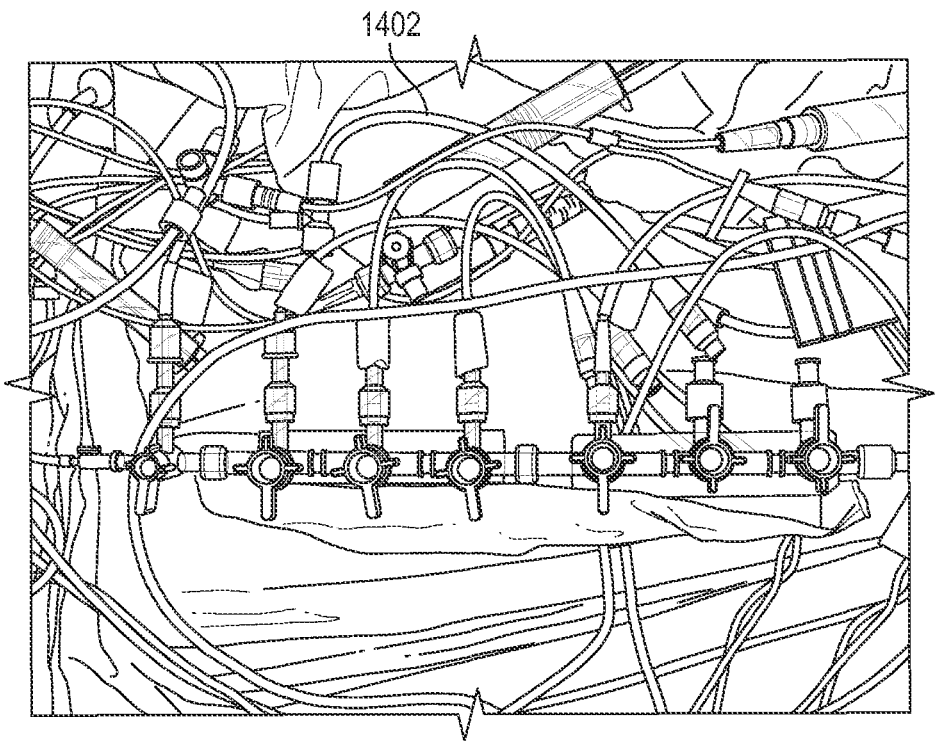
FIG. 14C is a perspective view of a medical device having tubing where a light emitter may be attached thereto to create an antimicrobial effect.
Figure 14D:
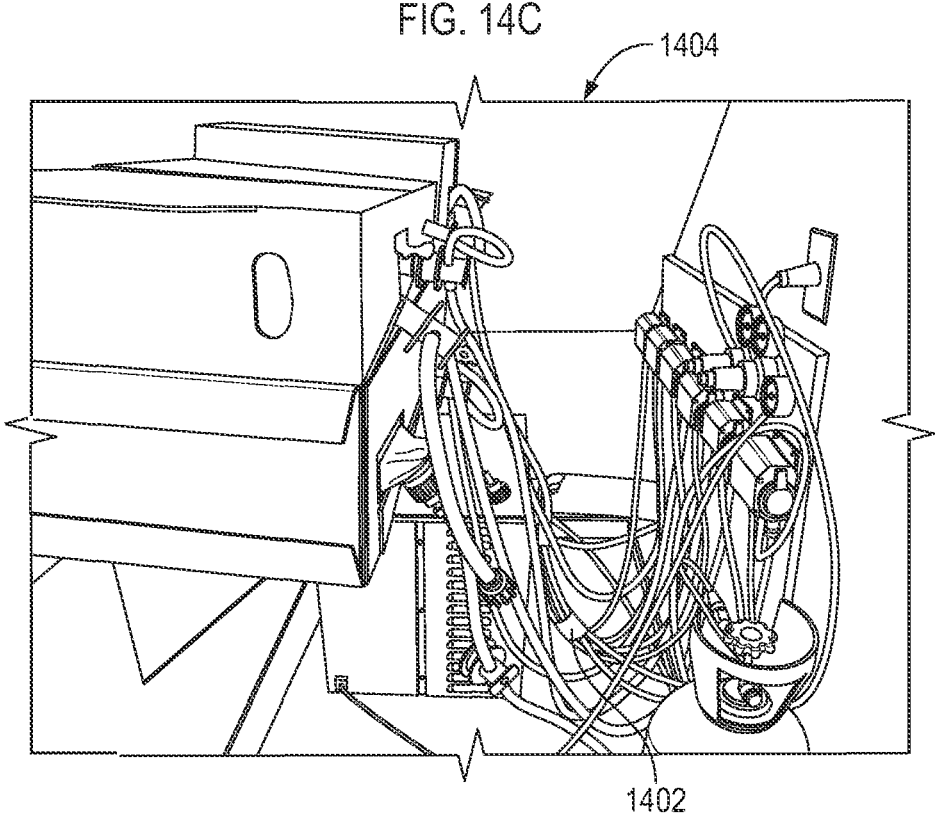
FIG. 14D is a perspective view of a beverage dispensing system with tubing that a light emitter may be attached thereto to create an antimicrobial effect.

Referring to FIGS. 14A-14D, another exemplary embodiment of use of a light emitter coupled to tubing 1402 with an optically transparent wall is illustrated generally at 1400. The light emitter 24 may be coupled to any tubing 1402 with an optically transparent wall where an antimicrobial effect is desired. As illustrated in FIGS. 14B and 14C, various external; tubing 1402 for delivery of fluids and gasses may be adapted as described herein. As illustrated in FIG. 14D, achieving an antimicrobial effect in tubing 1402 in the food service industry is also desirable, such as, for instance, a beverage dispensing system 1404.

In addition to medical applications, light-emitting antimicrobial tubing may have applications in other industries where control or prevention of microbial and fungal growth has applications, such as; energy production and delivery; material and chemical production; industrial machinery and equipment; automobile components; consumer durables and apparel; consumer staples, such as, food, beverages and tobacco retailing, and household products; pharmaceutical, biotechnology and life sciences;

Therefore, it can be seen that the present invention provides a unique solution to the problem of catheter-associated infections, by providing a catheter with an optically transparent wall and a light transmitter configured to emit any antimicrobial light, such as visible spectrum violet-blue 405 nm or 415 nm light, through the optically transparent wall. Because of the antimicrobial properties of violet-blue light, the risk of bacterial infection through the use of the catheter is reduced.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

The invention claimed is:

1. A catheter, tube, or instrument comprising:
a tube having light-transmissive walls with a distal portion configured for insertion into a patient and a proximal portion that remains external to the patient, the tube having at least one lumen for fluidic transport;
a tip at the distal portion for insertion of the tube into a patient at a skin insertion site;
a light source configured and embedded within the wall of the tube to emit safe, antimicrobial light throughout the light-transmissive walls to illuminate sites of microorganism colonization and potential sources of infection at the skin insertion site, within the lumen, and on an outer surface of the tube; and
wherein the tube is made from a material that transmits light through an inner surface and the outer surfaces of the tube, and further transmits light longitudinally down an axis of the tube.

2. The catheter, tube, or instrument of claim 1, further comprising a hub connected to the tube, the hub configured to transmit light emitted from the light source.

3. The catheter, tube, or instrument of claim 1, further comprising an optical fiber, wherein the optical fiber is side-emitting or side glow.

4. The catheter, tube, or instrument of claim 1, further comprising one or more optic fibers embedded in or adjacent to the wall of the tube.

5. The catheter, tube, or instrument of claim 4, wherein the one or more optical fibers are side-emitting or side glow.

6. The catheter, tube, or instrument of claim 1, wherein the emitted light is antimicrobial light of a wavelength not harmful to the patient.

7. The catheter, tube, or instrument of claim 1, wherein the emitted light is of wavelengths from 400 to 500 nm or 200 to 240 nm.

8. The catheter, tube, or instrument of claim 7, wherein the emitted light is of wavelengths of 405 nm or 415 nm.

9. The catheter, tube, or instrument of claim 7, wherein the emitted light is of wavelengths of 222 nm.

10. The catheter, tube, or instrument of claim 1, wherein the light source is positioned proximal to the tube to transmit the light through a length of the tube.

11. The catheter, tube, or instrument of claim 10 wherein the light source is positioned within or adjacent to a catheter hub.

12. The catheter, tube, or instrument of claim 1, further comprising one or more light transmitting or conducting filaments, wires, or threads, embedded in the walls of the tubing, adjacent to the walls of the tubing, or within the lumen of the tube.

13. The catheter, tube, or instrument of claim 12, wherein the optical light transmitting or conducting filaments, wires, or threads is electroluminescent wire or filament.

14. The catheter, tube, or instrument of claim 12, wherein the optical light transmitting or conducting filaments, wires, or threads is a glass-based fiber optic diffuser.

15. The catheter, tube, or instrument of claim 1, wherein the tube is made of safe, light-transmissive material of at least one of polymethyl methacrylate (PMMA), silica/quartz, thermoplastic polyurethane (TPU), flexible acrylic, transparent polyvinyl chloride (PVC), UV-inhibitor-free transparent PVC, or solar cell material.

16. The catheter, tube, or instrument of claim 1, wherein the light source is configured for emitting light circumferentially around the tube from the proximal portion and the distal portion.

17. The catheter, tube, or instrument of claim 1 further comprising a catheter access opening in fluidic communication with the lumen and adapted for fluidic engagement with the lumen for transporting fluid.

18. A method, comprising the steps of:
providing a catheter, tube, or instrument, including a tube having light transmitting walls, configured for insertion into a patient via a distal tip, and a proximal portion that remains external to the patient, the tube having at least one lumen for fluidic transport, and light transmitting walls adapted to distribute light both axially and in a side-emitting manner;
defining a light source configured and embedded within the wall of the tube to emit safe, antimicrobial light through the light transmitting walls of the tube, wherein the tube is made from a material that transmits light to an inner surface and an outer surface of the tube, and further transmits light longitudinally down an axis of the tube along a length of the tube; and
administering an antimicrobial light from the light source through the tube to eradicate bacteria and microorganism colonization at sites of potential colonization and infection including around a hub, at a skin insertion site, on the outer surface of the tube, and within the lumen.

19. The method of claim 18, wherein the catheter, tube, or instrument transmits tissue-safe, antimicrobial light.

20. The method of claim 18, wherein the step of administering an antimicrobial light comprises administering light in wavelengths from 400 to 500 nm or 200 to 240 nm.

21. The method of claim 18, wherein the step of administering an antimicrobial amount of light comprises administering light at a wavelength of 405 nm, 415 nm, or 222 nm.

22. The method of claim 18, wherein the step of administering an antimicrobial amount of light comprises administering light within the far UVC (ultra-violet-C) spectrum.

23. The method of claim 18, wherein antimicrobial effectiveness is achieved by optimizing the light by adjusting a parameter of the light emitter.

24. The method of claim 23, wherein the parameter is selected from the group consisting of: intensity, radiant exposure, dwell time, wavelength, duty cycle, and pulse frequency.

25. A method of manufacturing a catheter, tube, or instrument comprising:
a tube made of a safe, light-transmissive material of at least one of polymethyl methacrylate (PMMA), silica/quartz, thermoplastic polyurethane (TPU), flexible acrylic, transparent polyvinyl chloride (PVC), UV-inhibitor-free transparent PVC, or solar cell material, the tube having at least one lumen for fluidic transport,
a tip on a distal portion for insertion of the tube into a patient, while a proximal portion remains external to the patient;

defining a light source configured and embedded within the wall of the tube to emit safe, antimicrobial light throughout a light transmissive tube wall to illuminate sites of potential microorganism colonization and sources of infection at a skin insertion site, around a hub, within the lumen and on an outer surface of the tube, wherein the material transmits light through an inner surface and the outer surface of the tube and further transmits the light longitudinally down an axis of the tube along a length of the tube.

\* \* \* \* \*